(12) United States Patent
Barashkov et al.

(10) Patent No.: US 10,175,199 B2
(45) Date of Patent: Jan. 8, 2019

(54) TRACER PARTICLES, AND METHODS FOR MAKING SAME

(71) Applicant: Micro-Tracers, Inc., San Francisco, CA (US)

(72) Inventors: Nikolay Barashkov, Hercules, CA (US); Jonathan Germain, San Francisco, CA (US); David Eisenberg, San Francisco, CA (US); Zachary Eisenberg, San Francisco, CA (US); Lou Kish, Morgan Hill, CA (US)

(73) Assignee: Micro-Tracers, Inc., San Francisco, CA (US)

( * ) Notice: Subject to any disclaimer, the term of this patent is extended or adjusted under 35 U.S.C. 154(b) by 0 days.

(21) Appl. No.: 14/080,648

(22) Filed: Nov. 14, 2013

(65) Prior Publication Data

US 2014/0141085 A1    May 22, 2014

Related U.S. Application Data

(60) Provisional application No. 61/796,570, filed on Nov. 15, 2012, provisional application No. 61/851,244, filed on Mar. 4, 2013.

(51) Int. Cl.
*G01N 27/72*    (2006.01)
*G07D 7/04*    (2016.01)

(52) U.S. Cl.
CPC .............. *G01N 27/72* (2013.01); *G07D 7/04* (2013.01); *Y10T 428/2982* (2015.01)

(58) Field of Classification Search
CPC combination set(s) only.
See application file for complete search history.

(56) References Cited

U.S. PATENT DOCUMENTS

| | | |
|---|---|---|
| 2,868,644 A | 1/1959 | Eisenberg |
| 3,469,990 A | 9/1969 | Eisenberg |
| 4,029,820 A | 6/1977 | Eisenberg |
| 4,053,433 A | 10/1977 | Lee |
| 4,152,271 A | 5/1979 | Eisenberg |
| 4,188,408 A | 2/1980 | Eisenberg |
| 4,390,452 A * | 6/1983 | Stevens ............ G06K 19/06009 149/2 |
| 4,654,165 A | 3/1987 | Eisenberg |
| 5,512,131 A | 4/1996 | Kumar |
| 6,010,603 A | 1/2000 | Ye et al. |
| 6,140,226 A | 10/2000 | Grill et al. |
| 6,309,690 B1 | 10/2001 | Brogger et al. |
| 6,362,083 B1 | 3/2002 | Mueller-Fiedler et al. |
| 6,406,725 B1 | 6/2002 | Taylor |
| 6,647,649 B2 | 11/2003 | Hunt et al. |
| 6,773,812 B2 | 8/2004 | Chandler et al. |
| 6,796,504 B2 | 9/2004 | Robinson |
| 7,038,766 B2 | 5/2006 | Kerns et al. |
| 7,094,305 B2 | 8/2006 | Cleary |
| 7,126,755 B2 | 10/2006 | Moon et al. |
| 7,163,744 B2 | 1/2007 | Nightingale et al. |
| 7,288,320 B2 | 10/2007 | Steenblik et al. |
| 7,619,819 B2 | 11/2009 | Moon et al. |
| 7,807,468 B2 | 10/2010 | Bates |
| 7,874,489 B2 | 1/2011 | Mercolino |
| 7,964,407 B2 | 6/2011 | Bates |
| 8,069,782 B2 | 12/2011 | Fragala et al. |
| 8,247,018 B2 | 8/2012 | Mercolino |
| 8,263,129 B2 | 9/2012 | DeSimone et al. |
| 8,387,529 B2 | 3/2013 | Fragala et al. |
| 8,458,475 B2 | 6/2013 | Mercolino |
| 8,511,557 B2 | 8/2013 | Learmonth et al. |
| 9,127,181 B2 | 9/2015 | Yamauchi et al. |
| 9,223,235 B2 | 12/2015 | Yamauchi et al. |
| 9,383,648 B2 | 7/2016 | Sekine et al. |
| 2002/0122878 A1 | 9/2002 | Rosenberger |

(Continued)

FOREIGN PATENT DOCUMENTS

| | | |
|---|---|---|
| WO | 2001078087 | 7/2002 |
| WO | 2005111127 | 11/2005 |

(Continued)

OTHER PUBLICATIONS

Alocilja and Wang, "NanoBio Sensors and Integrated Microsystems for Intelligent Food Packaging," 2009 Symposium on Nanomaterials for Flexible Packaging. See slide No. 28.

(Continued)

*Primary Examiner* — Robert S Cabral
(74) *Attorney, Agent, or Firm* — Dergosits & Noah LLP

(57) ABSTRACT

The invention relates generally to tracer particles for product identification and/or authentication. When incorporated into a manufactured item, that item can be subsequently authenticated by either detecting, or failing to detect, the tracer particle. The tracer particles of the invention are magnetically attractable, with micromarkings, and in some embodiments, are manufactured with food grade materials and of a particle size suitable for ingestion by humans. The particles can be analyzed qualitatively or quantitatively. In other aspects, the invention provides methods for the manufacture of the tracer particles, and in other aspects, provides methods for using the particles. Examples of products that can be tagged using the tracer particles of the invention include pharmaceuticals, animal feeds or feed supplements, and baby formula. Other applications include forensics, such as in explosive materials.

15 Claims, 5 Drawing Sheets

(56) References Cited

U.S. PATENT DOCUMENTS

| | | |
|---|---|---|
| 2004/0098891 A1 | 5/2004 | Hunt et al. |
| 2005/0040222 A1 | 2/2005 | Robinson |
| 2005/0255599 A1 | 11/2005 | Wang et al. |
| 2005/0264001 A1 | 12/2005 | Kerns et al. |
| 2005/0265922 A1 | 12/2005 | Nie et al. |
| 2005/0277710 A1 | 12/2005 | Joyce et al. |
| 2007/0285782 A1 | 12/2007 | Stuck et al. |
| 2008/0042106 A1* | 2/2008 | Champ .................. C08F 2/32 252/408.1 |
| 2008/0199406 A1 | 8/2008 | Walter |
| 2008/0261011 A1 | 10/2008 | Benenati et al. |
| 2009/0068637 A1 | 3/2009 | Xia et al. |
| 2009/0220789 A1 | 9/2009 | DeSimone et al. |
| 2010/0046825 A1 | 2/2010 | Haushalter |
| 2010/0297027 A1 | 11/2010 | Loiret-Bernal et al. |
| 2010/0297448 A1 | 11/2010 | Walke |
| 2011/0111225 A1 | 6/2011 | Gabriele et al. |
| 2011/0147456 A1 | 6/2011 | Learmonth et al. |
| 2011/0147458 A1 | 6/2011 | Learmonth et al. |
| 2011/0217727 A1 | 9/2011 | Kim |
| 2011/0303564 A1 | 12/2011 | Pearson et al. |
| 2011/0303744 A1 | 12/2011 | O'Neill et al. |
| 2011/0303746 A1 | 12/2011 | Learmonth et al. |
| 2011/0304131 A1 | 12/2011 | Zhou et al. |
| 2012/0273564 A1 | 11/2012 | Mercolino et al. |
| 2013/0035422 A1 | 2/2013 | Freund et al. |
| 2013/0260301 A1 | 10/2013 | Yamauchi et al. |
| 2014/0001260 A1 | 1/2014 | Learmonth et al. |
| 2014/0028011 A1 | 1/2014 | Yamauchi et al. |
| 2014/0097245 A1 | 4/2014 | Learmonth et al. |
| 2014/0124398 A1 | 5/2014 | Mikels |
| 2014/0319815 A1 | 10/2014 | Sekine et al. |
| 2014/0346235 A1 | 11/2014 | Haupt |
| 2015/0060548 A1 | 3/2015 | O'Neill |
| 2015/0178738 A1 | 6/2015 | Learmonth et al. |
| 2017/0182838 A1 | 6/2017 | Wang et al. |

FOREIGN PATENT DOCUMENTS

| | | |
|---|---|---|
| WO | WO2005118650 A2 | 12/2005 |
| WO | WO2005124340 A1 | 12/2005 |
| WO | WO2006058247 A2 | 6/2006 |
| WO | WO2007002009 A2 | 1/2007 |
| WO | WO2007002016 A2 | 1/2007 |
| WO | WO2007021971 | 2/2007 |
| WO | WO2007021971 A2 | 2/2007 |
| WO | WO2007089753 A2 | 8/2007 |
| WO | WO2007095501 A2 | 8/2007 |
| WO | WO2007134192 A2 | 11/2007 |
| WO | WO2007149127 A1 | 12/2007 |
| WO | WO2011073354 A1 | 6/2011 |
| WO | WO2011159336 A1 | 12/2011 |
| WO | WO2011159337 A1 | 12/2011 |
| WO | WO2011159338 A1 | 12/2011 |
| WO | WO2011159339 A1 | 12/2011 |
| WO | 2012103476 | 8/2012 |
| WO | WO2014070958 A1 | 5/2014 |

OTHER PUBLICATIONS

Barashkov, N., Eisenberg D., Eisenberg S. and Mohnke, J., "Ferromagnetic Microtracers and Their Use in Feed Applications," on 8 pages, presented at the XII International Feed Technology Symposium in Novi Sad, Serbia, on Nov. 12-15, 2007.

Braeckmans et al., "Encoding microcarriers by spatial selective photobleaching," Nature Materials 2(3):169-173 (Mar. 2003).

Calderon et.al., Proceedings, Western Section, Amer. Soc. of Animal Science, v.51:1 (2000).

Chowdary et al., "A Review on Anti-Counterfeit Packaging and Use of ICT Tools to Combat the Issue of Counterfeiting," International Journal of Pharmaceutical & Biological Archives 3(4):706-711 (2012); retrieved from www.ijpba.info.

Deisingh, "Pharmaceutical counterfeiting," The Analyst 130, 271-279 (2005); www.rsc.org/analyst.

Dhar, "Anti-Counterfeit Packaging Technologies (Report): A strategic need for the Indian industry," a Study Report by Rajiv Dhar, Director, Indian Institute of Packaging (2009), from the (www.cii.in).

Eisenberg, "Microtracers™ F and their uses in assuring the quality of mixed formula feeds," Advances in Feed Technology, vol. 7, p. 78 (1992).

Eisenberg, "Validating cross-contamination control," Feed International, 1 (2006).

Eisenberg, "The use of Microtracers™ F (colored uniformly sized iron particles) in coding the presence of coccidiostats in poultry feeds," Zootechnica International, vol. 12, p. 46-50 (Dec. 1998).

Eisenberg, D., "Use of Microtracers® to Assure Feed Quality," Feed Manufacturing Technology Forum, Fujian Province, China (Apr. 11, 2012). Total of 102 slides. See slide Nos. 65 and 69.

Eisenberg, D., "The Use of Microtracers to Assure the Quality of Formula Feeds," Proceedings of the California Grain and Feed Association 2008 Conference, Monterey, CA (Jan. 16-17, 2008. Presentation contains 84 slides total. See slide No. 67.

Euliss, et al., "Imparting size, shape and composition control of materials for nanomedicine", Chem. Soc. Rev. 35:1095-1104 (2006).

Fayazpour et al., "Digitally Encoded Drug Tablets to Combat Counterfeiting," Advanced Materials 19:3854-3858 (2007).

Fayazpour, "Exploring New Applications for Photophysically Encoded Microcarriers," thesis submitted to obtain the degree of Doctor in Pharmaceutical Sciences, Ghent University, Faculty of Pharmaceutical Sciences (2008).

Finkel et al., "The Barcoding Microworld", Analytical Chemistry, 353A-359A (Oct. 1, 2004).

Forcinio, "Technology advances anticounterfeiting options," Pharmaceutical Technology p. 26 (Jun. 2002); retrieved from www.pharmtech.com.

Gómez-Martinez et al., "Different Barcodes Codification for Embryo Microlabeling" 14th International Conference on Miniaturized Systems for Chemistry and Life Sciences, Groningen, The Netherlands (Oct. 3-7, 2010), proceedings p. 1589-1591.

Gupta et al., "Counterfeit (Fake) Drugs & New Technologies to Identify it in India," (Review Article) International Journal of Pharmaceutical Sciences and Research vol. 3, Issue 11: 4057-4064 (2012).

Han et al., "Quantum-dot-tagged microbeads for multiplexed optical coding of biomolecules," Nature Biotechnology 19:631-635 (2001).

Han et al., "Drug Authentication Using High Capacity and Error-Correctable Encoded Microtaggants," 16th International Conference on Miniaturized Systems for Chemistry and Life Sciences, Okinawa, Japan (Oct. 28-Nov. 1, 2012).

Han et al., "Lithographically encoded polymer microtaggant using high-capacity and error-correctable QR code for anti-counterfeiting of drugs," Advanced Materials 24(44):5924-5929 (ePub Aug. 28, 2012).

Huang et al., "Unbreakable codes in electrospun fibers stop medicine counterfeiting," Journal of Controlled Release 148(1). p. e13-e15 (2010).

Kumar and Whitesides, "Features of Gold Having Micrometer to Centimeter Dimensions Can Be Formed through a Combination of Stamping with an Elastomeric Stamp and an Alkanethiol Ink Followed by Chemical Etching," Appl. Phys. Lett., v.63, p. 2002-2004 (1993).

Power, "Anti-Counterfeit Technologies for the Protection of Medicines," a publication by the World Health Organization, from the International Medical Products Anti-Counterfeiting Taskforce (IMPACT), retrieved from www.who.int/impact/events/IMPACT-ACTechnologiesv3LIS.pdf; date unknown.

Product & Image Security Foundation, "Authentication Made Simple," Newsletter of the Product & Image Security Foundation, No. 85 (May/Jun. 2012). Retrieved from www.productandimagesecurity.org.

Qin et al., "Soft lithography for micro- and nanoscale patterning," Nature Protocols vol. 5, No. 3, pp. 491-502 (2010; published online Feb. 18, 2010).

(56) References Cited

OTHER PUBLICATIONS

Ruiz and Chen, "Microcontact printing: A tool to pattern," Soft Matter (The Royal Society of Chemistry), 3:1-11 (2007).
Shah et al., "Anticounterfeit packaging technologies," J Adv Pharm Technol Res. 1(4): 368-373 (Oct.-Dec. 2010).
Stealth Mark Technology description, on 7 pages, date of availability unknown, retrieved from www.stealthmark.com.
Talati et al., "Pharmaceutical Counterfeiting and Analytical Authentication," Current Pharmaceutical Analysis vol. 7, No. 1, pp. 54-61 (Feb. 2011).
U.S. Food and Drug Administration (USFDA), "Guidance for Industry: Incorporation of Physical-Chemical Identifiers into Solid Oral Dosage Form Drug Products for Anticounterfeiting," US Govt Document No. UCM171575 (2011); accessed at www.fda.gov/downloads/Drugs/GuidanceComplianceRegulatoryInformation/Guidances/UCM171575.
Winter, "Edible Bar Codes Aim to Swallow the Counterfeit Drug Market," Bloomberg Businessweek, www.businessweek.com, Sep. 4, 2013.
Wong, "Edible Bar Codes for Supplement Tracking, Authentication," accessed from http://www.naturalproductsinsider.com/ (posted on: Apr. 10, 2013).
Wong, "Anti-Counterfeiting: On-dose authentication: Walking softly, prepared to stick," Tablets & Capsules vol. 9, No. 2: p. 28-33 (Mar. 2011).
Wu, "Tagged Out: New markers for explosives may lay old safety questions to rest," Science News Online (Sep. 14, 1996).
Zadbuke et al., "Recent trends and future of pharmaceutical packaging technology," J Pharmacology & BioAllied Sciences vol. 5, Issue 2, p. 98-110 (2013).
Zhi et al., "Micromachining microcarrier-based biomolecular encoding for miniaturized and multiplexed immunoassay," Analytical Chemistry 75(16):4125-4131 (Aug. 15, 2003).
Zinn, "A guide to feed mixing," Research Updates and Reports, Desert Research and Extension Center, Department of Animal Science, Univ. of California Davis (1999).
Holmes et al., "Fabrication of buried channel waveguides on silicon substrates using spin on glass," Appl. Opt., v.32, p. 4916-4921 (1993). Abstract only.
Huang et al., "Unbreakable Codes in Electrospun Fibers: Digitally Encoded Polymers to Stop Medicine Counterfeiting," Advanced Materials vol. 22(24):2657-2662 (2010). Abstract only.
Li, "Technology designed to combat fakes in the global supply chain," Business Horizons Special Issue: Protecting Your Intellectual Property Rights, vol. 56, Issue 2, Mar.-Apr. 2013, pp. 167-177. Abstract only.
Libioulle et al., "Contact inking PDMS stamps for microcontact printing alkanethiols on gold," Langmuir, v.15, 300-304 (1999). Abstract only.
Lorenz et al., "SU-8: a low-cost negative resist for MEMS," J. Micromech. Microeng., v.7, p. 121-124 (1997). Abstract only.
Murthy et al., "Evaluation of mixer efficiency test," Indian J. Animal Nutr., v. 7(2):159 (1990). Abstract only.
Quist et al., "Recent Advances in Microcontact Printing," Anal. Bioanal. Chem., v.381:591-600 (2005). Abstract only.
Platek et al., "Applications of Microscopy and Microanalysis in USFDA Forensic Cases," Microscopy and Microanalysis vol. 15 (Suppl. 2), pp. 796-797 (published online Jul. 25, 2009). Citation only.
International Search Report and Written Opinion dated Apr. 9, 2014 in corresponding International Application No. PCT/US2013/070185 (now published as WO2014/078589).
Supplementary European Search Report and European Search Opinion for European Patent Appl. No. EP13855694.9, dated Jun. 20, 2016; on 9 pages.
CN 86102668A Limited English language translation of bibliographic data and abstract; information retrieved from <worldwide.espacenet.com> and <www.google.com/?tbm=pts&gws_rd=ssl>.
CN 101379397 Limited English language translation of bibliographic data and abstract; information retrieved from <worldwide.espacenet.com> and <www.google.com/?tbm=pts&gws_rd=ssl>.
CN 1360213A Limited English language translation of bibliographic data and abstract; information retrieved from <worldwide.espacenet.com> and <www.google.com/?tbm=pts&gws_rd=ssl>.
CN 1166964C Limited English language translation of bibliographic data and abstract; information retrieved from <worldwide.espacenet.com> and <www.google.com/?tbm=pts&gws_rd=ssl>.
CN 102608327A Limited English language translation of bibliographic data and abstract; information retrieved from <worldwide.espacenet.com> and <www.google.com/?tbm=pts&gws_rd=ssl>.
Communication from the European Patent Office containing an Examination Report with Search Opinion, Communication dated Jan. 18, 2018, in regard to EPO Patent Application No. 13855694.9, on 4 pages total.
Granted Chinese Patent No. ZL201380059664.9, with accompanying Patent Certificate of Invention No. 2807464, issued on Feb. 6, 2018. Granted Chinese Patent is a National Entry arising from PCT International Patent Application Serial No. PCT/US2013/070185. Total 39 pages.
English translation of Chinese Patent Certificate of Invention No. 2807464, dated Feb. 6, 2018, describing the grant and issuance of Chinese Patent No. ZL201380059664.9. One page.

* cited by examiner

TRACER PARTICLES, AND METHODS FOR MAKING SAME

CROSS-REFERENCE TO RELATED APPLICATIONS

This application claims benefit of U.S. Provisional Application Ser. Nos. 61/796,570, filed Nov. 15, 2012, and 61/851,244, filed Mar. 4, 2013, both of which are herein incorporated by reference in their entirety.

FIELD OF THE INVENTION

The invention relates generally to tracer particles, and methods for making the tracer particles. The tracer particles described herein find a variety of uses, for example, for tagging manufactured items that can be subsequently authenticated by either detecting, or failing to detect, the tracer particle in the item at any point post-manufacture. Examples of products that can be tagged using the tracer particles of the invention include pharmaceuticals, animal feeds or feed supplements, and baby formula. Other applications include forensics, such as for tracing the source of materials used to manufacture explosives.

BACKGROUND OF THE INVENTION

Counterfeit products pose a major threat in many industries, both in the form of public safety as well as pecuniary losses. One industry facing the wide-spread problems of counterfeiting is the pharmaceutical industry. The challenges of controlling counterfeit drugs have increased as pharmaceutical markets become more international. For example, drug manufacturing can involve importing materials from other countries, in addition to distributing finished products across international borders. As a result, additional handlers, repackagers and distributors in a variety of locations are required in the product supply chains, thereby rendering proprietary drugs even more vulnerable to tampering and fraud. These complex supply chains create entry points through which contaminated, adulterated and counterfeit products can infiltrate the drug supply.

Counterfeiting activities in oral pharmaceuticals can take various forms, such as (i) entirely fraudulent products containing no active ingredient, (ii) diluted, generic or insufficient dosages of the active ingredient, contrary to the labeled dosages on the packaging or (iii) substitution of the intended active ingredient with a different or inferior drug to elicit a similar physiological response. In addition, some fraudulent pharmaceuticals contain harmful or toxic ingredients. Counterfeit pharmaceutical products that fail to deliver critical active ingredients, or inflict toxic effects, pose a significant threat to public safety.

There are documented cases of counterfeiters targeting a wide range of prescription and non-prescription products, such as vaccines, cough syrup, anti-malarial drugs, heparin, painkillers, blood thinners, dietary supplements, teething medicines, hypertensive medicines, steroids. Products that are expensive and/or high demand in underdeveloped countries are attractive targets for counterfeiting activity. Counterfeit drugs can lead to illness, increased health risks and in extreme cases involving diethylene glycol (DEG) and melamine, have been fatal.

Governmental regulatory agencies, both in the U.S. and abroad, have struggled to detect, prevent, and address drug contamination and counterfeiting issues. Limited governmental resources and a lack of international consensus have hindered the implementation of global, uniform drug control practices. In order to be effective, agencies need to agree on what constitutes a counterfeit drug, the high-risk proprietary drugs, product traceability and authentication systems and sampling/testing protocols at international borders. Undeveloped and underdeveloped nations are particularly vulnerable to the activities of drug counterfeiters.

The pharmaceutical industry has focused on unique packaging that allow the end users to discern authentic from counterfeit products. These efforts have included barcodes, holographic labels, laser encrypted labels, color shifting security ink, and DNA reagent markers. Ideally, these packaging security features should be easily identifiable, yet difficult to duplicate. Unfortunately, over time, increasingly sophisticated forgery efforts have adapted many of these package security measures.

In addition to marking drug packaging the actual drugs can be marked with a security feature to authenticate the product. This direct marking approach has various benefits. If a legitimate drug manufacturer is able to mark his pharmaceutical product with an identifying physical tag at the time of manufacture, this will enable a health professional to determine if the drug is genuine at any point post-production. Such drug "tracers" are called tags, microtags, taggants, markers and/or microparticles. Detection, or lack thereof, of these tracers in a pharmacutical product will ideally serve as a marker to indicate drug authenticity or drug fraudulence, respectively.

The need for security control measures to thwart counterfeiting and product tampering extend to a variety of industries, including various foods and other types of consumables. Well known examples of counterfeiting and tampering exist in powdered and liquid baby formula, animal feed, pet foods, cigarettes, plastics and replacement airbags. There is also a need for tracer particles in forensic applications, such as coding for the source of explosive materials.

Various tagging technologies for the authentication of marked goods have been proposed, including systems for drug marking and drug tracing. Tracers have also been described for coding the source of dynamite and black powder. However, these proposed systems have various drawbacks. Limitations of these existing tracer systems include the large sizes of the tracer particles, making them unsuitable in applications such as coding human pharmaceuticals. Other significant limitations in the tracer particles art include particles that are not suitable for human or animal ingestion, tracers that are expensive to produce, and the analytical procedures to detect and/or quantify such tracers either have not been developed, are expensive, are time consuming, are not readily portable, or require materials or reagents that are not readily available.

What is needed in the art are improved tracer particles and associated techniques for monitoring counterfeit/fraudulent products, or products that have been subject to tampering. Ideally, these improved systems will permit cost-effective sampling and testing for product integrity. Also what is needed in the art are tracers that are suitable for ingestion.

What is needed in the art are improved tracer particles that can be added directly to an oral pharmaceutical formulation at the time of manufacture, in parallel with the active ingredient. This type of drug tracer should be undetectable or sufficiently complex to thwart counterfeiters from detecting or reproducing the tracer particles. Ideally, methods for detection of the tracer in the manufactured product should be non-complex and use equipment that is readily available and ideally also portable. Such drug tracers will permit determination of pharmaceutical authenticity anywhere along the post-production stream of commerce. Optionally, this type of authenticity control can be done covertly by the drug manufacturer.

The present invention, in its many embodiments, provides compositions and methods for product security that overcome challenges in the industry, and provide many benefits previously unrealized in other types of security products. In addition, still further benefits flow from the invention described herein, as will be apparent upon reading the present disclosure.

SUMMARY OF THE INVENTION

The invention described herein provides compositions, and methods for producing those compositions, that solve industry problems associated with monitoring product security and detecting counterfeit or tampered goods. The invention has diverse applications, including the field of counterfeit pharmaceutical detection.

The invention provides tracer particles that find a variety of uses. The particles are magnetic, and are characterized by at least one distinguishing marking on the surface of the particle, where the marking does not exceed about 40 microns in any dimension. Particles with smaller markings are also provided for example, with markings that do not exceed about 20 microns in size. Particles with markings between about 500 nanometers and about 20 microns are also provided. The magnetic particles can be any desired size, for example, not exceeding about 400 microns in any dimension, or smaller particles such as not exceeding about 100 microns or about 50 microns in size. The magnetic material in the particles can be any magnetic material, for example, iron, nickel, gamma-ferrioxide, ferrites, or any combinations of materials. The markings used on the tracer particles can be alphanumeric characters, but are not limited to alphanumeric characters. The tracer particles can optionally contain additional features that facilitate detection and analysis, such as a fluorescent material, a thermochromic material, a chromogenic material or any type of chromophore.

The tracer particles can be incorporated into any of a variety of products to generate marked articles that can later be authenticated, including marked pharmaceutical products.

When a marked pharmaceutical product is generated, that marked product contains at least one excipient from the drug manufacture process, and the tracer particles that are dispersed in the pharmaceutical product, or can be localized in the pharmaceutical product, such as in a tablet coating. In some embodiments of marked pharmaceutical products, the tracer particles in the product are preferably smaller than about 100 microns in any dimension, or smaller, for example, smaller than about 80 microns or smaller than about 50 microns. When producing a particle that is smaller than about 100, or 80 or 50 microns in size for pharmaceutical use, the distinguishing marking on that particle can be markings that do not exceed about 10 microns in any dimension, but in preferred embodiments, smaller markings, for example smaller than about 5 microns or 2 microns can be used. When used in the pharmaceuticals, the particles are ingestible, and are made from materials generally regarded as safe for human consumption. The tagged pharmaceuticals can be in solid formulations or liquid formulations.

Tracer particles of the invention can also be used to produce marked animal feeds, such as formula feeds. The magnetic tracer particles are incorporated into the bulk matter feed mix. That feed mix can later be tested and authenticated by ascertaining the presence or absence of the tracer particles. The tracer particles used to generate the tagged animal feed can be limited to particles not more than about 350 microns in size. The markings on the particles are generally not larger than about 40 microns, although smaller particle populations can also be used.

The invention provides a generalized method for producing marked products, where the method consists essentially of dispersing the magnetic tracer particles throughout a flowable bulk material. The particles are not particularly limited in size, but may be restricted to particles smaller than about 400 microns, or smaller than about 100 microns or 50 microns. In some instances, the size of the magnetic particles that are used is a bracketed range, for example, between about 35 and 50 microns, or between about 50 and 80 microns, or between 80 and 150 microns, or between 250 and 400 microns. The particles used to make the marked products generally contain at least one distinguishing mark that is not larger than about 40 microns in any dimension, although smaller size markings such as smaller than 20 microns, may be preferable. The flowable bulk material can be dry bulk particulate material or liquid bulk material. Examples of marked products includes pharmaceuticals (human and animal), baby formula powder, premixed liquid baby formula, explosives, animal feed, and an animal feed premix.

The magnetic particles are used in a wide variety of security applications, most notably, to authenticate a product that has been tagged with the tracer particles. Generally, the method for authenticating a product first starts with the manufacture of a marked product using the tracer particles as described above. A product can be tested for authenticity any point after production by detecting the tracer particle in the bulk material of the product, or in an article formed from the bulk material. If the tracer particle is detected in the tested product, authenticity of that product is confirmed. The detecting step will involve more than one step, where generally, the first step is to isolate the tracer particles using magnetic separation, and a second step of visualization of the distinguishing mark on the surface of the tracer particle, generally using magnification such as from a low power microscope capable of observing surfaces of opaque objects using incident light. Visualizing the particles can be facilitated by using a secondary detection mechanism that has been installed in or on the particles, such as by the addition of any suitable chromogenic or fluorogenic materials, or suitable chromophores or fluorophores into or on the particles. Such materials can then be used to visualize the particles by colorimetric detection or fluorometric detection, either visually or electronically detected.

The tracer particles of the invention are produced using photolithography based methodologies. In its simplest application, the magnetic tracer particles are produced using a traditional photolithography technique. This method generally follows the steps of (i) attaching a magnetic metal or metal containing substrate layer to an underlying support layer; (ii) wet etching the substrate layer to produce many copies of a distinguishing mark on the surface of the substrate layer; (iii) removing the marked substrate layer from the support layer; and (iv) fragmenting the marked substrate layer into particles, where the majority of particles are expected to contain at least one copy of the distinguishing mark on the surface of the particle. Particles of a desired size with markings of specified dimensions can be produced.

In a variant method, microcontact printing is used to produce the tracer particles. This method generally follows the steps of (i) creating a master template from iron, steel or silicone, and etching many copies of a distinguishing mark on the surface of the master template, (ii) making an elastomeric stamp from the master template, (iii) imprinting the marks that are on the stamp onto a magnetic substrate layer by contacting the stamp to the magnetic substrate layer with a suitable ink, (iv) wet etching the magnetic substrate layer according to the ink imprint, and (v) removing the magnetic substrate layer as a sheet and fragmenting the sheet into a powder or granular state, thereby making the tracer particles. The substrate layer from which the tracer particles are formed can be a metal layer, such as an iron foil, or can be a polymer film containing a magnetic powder additive.

In a third method, plasma etching is used to produce the magnetic tracer particles. This method generally follows the steps of (i) providing a magnetic metal (such as an iron foil) or a magnetic metal-containing substrate layer (such as a polymer that contains an iron powder) that is attached to an underlying support layer; (ii) plasma etching the substrate layer to produce many copies of a distinguishing mark on the surface of the substrate layer; (iii) plasma etching the marked substrate layer to a depth that is the full thickness of the substrate in a pattern that separates the distinguishing marks on the surface of the substrate from each other; and (iv) detaching the substrate layer from the underlying support, thereby releasing the magnetic tracer particles. The sizes of the particles produced are not particularly limited, except that this plasma etching can produce generally higher resolution compared to microcontact printing, permitting smaller particle sizes (for example, smaller than about 50 microns or about 100 microns) and smaller distinguishing marks (for example, smaller than about 20 microns, or 10 microns, or 2 microns).

BRIEF DESCRIPTION OF THE DRAWINGS

FIG. 1A provides a schematic illustrating the theory of positive working photoresist. FIG. 1B provides a schematic illustrating the theory of negative working photoresist.

DETAILED DESCRIPTION OF THE INVENTION

Figure 1A:
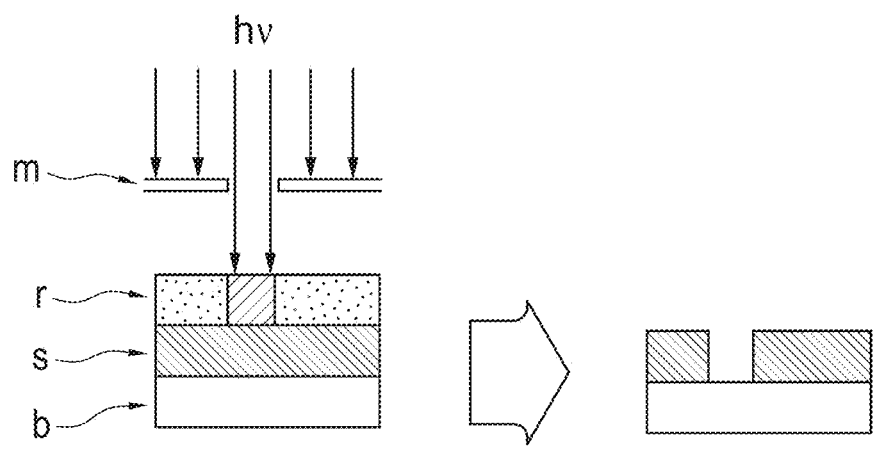
FIGS. 1A and 1B provide schematics illustrating the theory of traditional photolithography.

The present invention provides tracer particles, as well as methods for the production of the tracer particles. These tracer particles, and the methods for making the same, have a number of advantages over the state of the art, and have a wide variety of applications, which will be apparent from the present disclosure.

Most generally, the tracer particles of the invention are small (e.g., not larger than about 400 micrometers (i.e., microns) in any one dimension, and can be used, for example, in formula feeds. In other embodiments, the particles are not larger than about 100 microns in any one dimension, and can be used, for example, in human pharmaceuticals. Particles having still larger or smaller dimensions, of any specified desired size, are also contemplated. In some embodiments, the particles comprise only food grade materials, and are less than about 100 microns in size. In other aspects, the particles are magnetically attractable to facilitate their isolation for analysis. The particles can be further coded with fluorescent compounds to facilitate their analysis.

At least one surface of the particle contains some type of intentional marking, for example but not limited to alphanumeric characters, where the size and/or content of the marking will permit that marking to serve as an authenticating security feature. For example, a marking that is not larger than about 40 microns in any dimension, such as a letter that is not larger than 40 microns in width or height, can serve as an authenticating feature. Such a marked particle can serve as an authentication tag because illicit duplication of that particle containing that character (e.g., production by a counterfeiter) is highly unlikely due to the sophistication required to produce the marked particle. Markings of still smaller dimensions are also available, for example, not larger than about 20 microns in any dimension, or 5 microns, or 2 microns, or 500 nanometers.

The tracer particles of the invention are used to mark various products, where the tracer particles are incorporated into the product at the time of manufacture of the article. The tracer particle will then serve as an authentication tag to determine whether or not any given article in the stream of commerce is authentic (i.e., contains the tracer particle) or counterfeit (i.e., does not contain the tracer particle), or has been subjected to tampering (i.e., may contain quantitatively fewer detectable tracer particles as compared to the number of detectable tracer parties that would be expected in an authentic item). Still other uses for these tracer particles includes quantifying mixing efficiency in formula feeds and other bulk materials, monitoring cross contamination and the assessing the presence or absence of coded microingredients.

In some embodiments, tagged products are formed from flowable dry bulk particulate materials such as powders or granulated materials, or any mixtures of such materials, and the end product of the manufacturing process remains in a flowable bulk particulate form, for example, infant/baby formula powders, explosives, animal feeds and animal feed premixes or feed supplements. As used herein, the terms "flowable," "flowability" or "flowing" or similar expressions describe materials that have the capacity to move by flow in a manner typically characterized by liquids. These terms can refer to solids that are in a loose particulate state, such as powders or a granulated state.

However, it is not intended that the tagged products must remain in a flowable bulk particulate state. In some aspects of the invention, products formed from the tagged dry bulk particulate material do not remain in a flowable particulate state. For example, the manufacture of tablet style oral pharmaceuticals starts with combining and mixing various dry bulk particulate materials, and then subjecting the mixture to various processes and conditions that result in a hardened solid object (e.g., a tablet style pill). The tablet has lost the dry bulk particulate properties of the starting materials, however, still comprises the tracer particle dispersed within the hardened bulk material. This resulting solid pill that has been tagged with a tracer particle of the invention is within the scope of the invention. The tracer particles of the invention find use in producing many types of tagged pharmaceutical products.

In other embodiments, the tracer particles are used to tag bulk materials that have lost their flowable properties, and are transformed to solid objects. For example, this includes pharmaceuticals that are in a solid tablet form, and also includes polymers such as plastics that are used in high-risk markets such as electronics, medical products, aviation and automotive industries.

It is not intended that the products that are tagged with the tracer particles be limited to dry bulk particulate materials, or solid objects formed from the dry bulk material. In other aspects of the invention, the products that are tagged with the tracer particles can be in a liquid form, or behave as a liquid. The use of flowable liquids as bulk material (e.g., liquid excipients) to produce products such as medicines for oral delivery are known in the art and within the scope of the invention. The liquid excipients that find use with the invention are not limited, and can comprise aqueous or non-aqueous liquids, organic liquids such as some types of organic solvents, combinations of materials that behave as liquids, such as colloids, suspensions and slurries, and liquefiable materials such as lipids.

The invention also provides methods for producing the tracer particles of the invention. These methods use modified photolithography techniques, and can incorporate both wet etching and dry etching (plasma etching) protocols.

I. Magnetic Tracer Particles

The tracer particles of the invention are magnetic, i.e., they comprise at least one magnetic material in sufficient quantity to render the particle magnetic, i.e., magnetically isolatable. The production and use of magnetic tracer particles facilitates isolation of the particles from bulk material, such as from pharmaceuticals that have been ground to powder form, or from animal feed or feed supplements that are in bulk particulate or granular form. Tracer particles of the invention can be produced from any suitable magnetic material, and are not limited in that aspect.

Magnetic materials are, most generally, materials that display magnetism when in the presence of a magnetic field or in the presence of other magnets. Particles of the invention can be magnetic due to the presence of permanent magnet materials, which have persistent magnetic moments (creates its own magnetic field) caused by ferromagnetism. Ferromagnetic and ferrimagnetic materials, which are the materials commonly referred to as "magnetic," are attracted to a magnet, and can retain magnetization to become magnets. Ferromagnetic materials include nickel, iron, cobalt, gadolinium and their alloys. Ferrimagnetic materials, which include the alloys alnico, ferrites, magnetite and lodestone, differ from ferromagnetic materials in their microscopic structure.

Particles of the invention can also be magnetic due to the presence of paramagnetic, or superparamagnetic, materials. Paramagnetic materials also display magnetic properties when placed in a magnetic field, and are attracted to a magnetic field, but these materials do not retain any residual magnetism once removed from the magnetic field.

In some embodiments of the invention, the tracer particles are manufactured directly from metal sheet substrates, such as iron sheets or steel sheets, often in the form of a foil. These particles thus produced are magnetic due to the metal used to form the substrate.

In other embodiments, the magnetic tracer particles can be produced from polymer substrates, for example, food grade polymers, that have been supplemented with a magnetic material such as a magnetic powder. Sufficient magnetic material is added to the polymer matrix to produce polymer matrix particles that display magnetism when placed in a magnetic field. The magnetic supplements can be, for example, a ferromagnetic material, such as powders of iron, nickel, gamma-ferrioxide, ferrites, reduced iron, electrolytic iron, iron oxide or some types of stainless steel. The choice of any particular magnetic material to form a magnetic polymer tracer particle is not limiting. For example, magnetic powders of various size particles, compositions, and from various manufactures can be used.

In some embodiments, magnetic powder particle sizes can vary, for example, between about one (1) and six (6) microns in size, but larger or small magnetic material grains can also be used. Magnetic powder supplement concentration ranges of 3-10% by weight can be sufficient to produce the magnetic polymer particles. Various commercial magnetic powder products can be used, for example, iron particles with sizes between 1-6 microns (Goodfellow Group; Coraopolis, Pa.), reduced iron with particles sizes below 325 mesh, i.e., below 44 microns in size (North American Hoganas; Niagara Falls, N.Y.) or iron oxide with particles sizes below 5 microns (Sigma-Aldrich; St. Louis, Mo.).

The magnetic tracer particles of the invention can be conveniently isolated from a source material using a simple magnetic device, or by using commercially available devices designed for the collection of magnetic particles from a bulk material, for example, a laboratory magnetic separator such as the MicroTracer, Inc. Rotary Detector™, or a rare earth magnetic probe (e.g., MSP100 Probe, 4B Components; Morton, Ill.).

In some embodiments, the magnetic tracer particles of the invention are dispersed in a solid article, such as a pharmaceutical tablet. In this case, the particles can be isolated by grinding or pulverizing the solid tablet to form a finely grained powder, and the particles can be separated from that powder by using any suitable apparatus for isolation of magnetic particles from dry material. In some embodiments, the magnetic tracer particles of the invention are dispersed in a liquid or liquid-like product, such as a liquid-containing capsule, a liquid medication, or a colloid, suspension or slurry. In this case, the particles can be isolated by a device such as a magnetic wand.

II. Tracer Particle Dimensions

The present invention provides tracer particles that can be produced to any desired size. In some embodiments, it is desirable to specify a particular sized particle that is optimized for the various applications where they find utility. The invention provides methods for producing tracer particles of any desired size. For example, particles not larger than about 400 microns in any one dimension are provided. That is to say, the particles do not have any dimension larger than about 400 microns. Alternatively, particles not larger than about 100 microns, 50 microns, 10 microns or 5 microns can also be produced.

As described herein, methods for producing the marked tracer particles can use traditional photolithography, as well as microcontact printing variations of photolithography. See EXAMPLES 1, 2 and 3. When those methods are used, the final etching step produces an intact sheet or disk that contains numerous etched copies of the distinguishing mark, but where the intact sheet then needs to be dissociated to produce a plurality of particles, where each particle, or the majority of particles, contain at least one copy of the distinguishing mark. When using these photolithography methods, the intact sheet of material can be either an metal foil sheet, such as an iron sheet, or a sheet of a polymer that is embedded with a magnetic powder, such as an iron powder.

In some aspects, the size of the particle is determined by the use of mesh screens, as known in the art. This is accomplished by taking the intact printed sheet of material containing multiple copies of the etched mark, and dissociating that material with any suitable device to grind or disintegrate the sheet. In some aspects, any device analogous to a coffee bean grinder can be used, where the material is exposed to spinning blades or any other type of mechanical agitation for an amount of time sufficient to disintegrate the starting material to produce a powder or granular consistency. The powder is then sifted through one, or a combination of, mesh screens having a specified mesh pore dimension.

A mesh size designation is the number of openings in one linear inch of mesh. As the mesh size designation increases, the size of the pores in the sieving screen decreases. Particles having dimensions smaller than the sieve opening size will pass through the mesh, and particles having dimensions larger than the opening size will be retained and do not pass through the mesh. By sequentially using two different size screens, a population of particles can be isolated having an upper and lower size limit.

A number of mesh types and sizes are available from various manufacturers. Typical mesh sizing is provided in the table below. Any of these mesh sizes finds use with the invention to produce tracer particles having a defined size or size range.

| Mesh Sieve Size (number of mesh openings in one linear inch of mesh) | Size of the Mesh Openings (microns) | Size of the Mesh Openings (inches) |
|---|---|---|
| 30 | 595 | 0.0232 |
| 35 | 500 | 0.0197 |
| 40 | 420 | 0.0165 |
| 45 | 354 | 0.0138 |
| 50 | 297 | 0.0117 |
| 60 | 250 | 0.0098 |
| 70 | 210 | 0.0083 |
| 80 | 177 | 0.007 |
| 100 | 149 | 0.0059 |
| 120 | 125 | 0.0049 |
| 140 | 105 | 0.0041 |
| 170 | 88 | 0.0035 |
| 200 | 74 | 0.0029 |
| 230 | 63 | 0.0024 |
| 270 | 53 | 0.0021 |
| 325 | 44 | 0.0017 |
| 400 | 37 | 0.0015 |

In other embodiments of the invention, the particles are produced using a reactive plasma etching procedure. See EXAMPLE 4. In some embodiments, when using this procedure, the size of the tracer particles are determined by the plasma etch process, where the substrate is etched with both the distinguishing mark, as well as etched completely through the magnetic polymer substrate layer around its circumference, resulting in the separation of individual particles of fixed length and width dimensions. In other embodiments of the plasma etching methodology, the plasma etch does not completely penetrate the full thickness of the substrate layer. In that case, the plasma etched material can be produced as a sheet, and that sheet is then processed in a grinder and sifted through one or more mesh screens to produce particles of defined sizes.

The sizes of the tracer particles are customizable. In some aspects, particles having an upper size limit are preferred. For example, the invention provides particles that do not exceed about 400 microns, or about 420 microns in any dimension. In other embodiments, the particles do not exceed about 350, 300, 200, 100, 80 or 50 microns in any dimension. Still larger particles are also provided. In some embodiments, the present invention is not bounded by an upper limit of the particle size. For example, particles can be larger than about 300 microns, 400 microns or 500 microns in dimension.

In other preferred embodiments, tracer particle sizes are provided in a bounded size range. For example, the invention provides particle populations that are between about 250 and 420 microns, or between about 250 and 400 microns. Other useful ranges can be, for example, between about 50 and 80, or between about 80 and 100 microns, or between about 88 and 105 microns, or between about 74 and 105 microns. Any preferred size range population can be specified. The size specifications are not limited to commercially available mesh screen sizes, because the plasma etching methods of the invention have the ability to produce tracer particles of any desired size.

The preferred size of the tracer particles of the invention is generally determined by the intended use of the particles. In some aspects, particles having sizes not exceeding about 50 microns, or about 80 microns, or about 100 microns are generally preferred, and find particular use in human consumables, such as in pharmaceutical products and in powder or liquid baby formulas. Larger particles, i.e., particles with a larger upper size limit, also find use, for example, in applications that are not as stringent with regard to particle size limitations, such as in animal feeds and in explosives. These larger particles can have sizes that do not exceed, for example, about 200 microns, 210 microns, 250 microns, 297 microns, 300 microns, 350 microns, 354 microns, 400 microns, 420 microns, 500 microns, or 595 microns, and can also be produced as populations of particles having upper and lower size limits.

III. Tracer Particle Markings

The present invention provides tracer particles that can be produced in any desired size, and further, where the particles contain at least one distinguishing mark on the surface of the particle. This mark is generated by an etching process that can utilize either traditional photolithography wet etching, or by a reactive plasma etching process. The size and nature of the etched mark can be optimally selected for the intended application for the tracer particle.

As used herein, the expressions "mark," "marking," "distinguishing mark," "identifying marking" or similar terms refer to a single intentional mark on the surface of the tracer particle. In some embodiments, the mark is a single alphanumeric character, for example, the letter "M" or the number "5." As used herein, the expression "maximal dimension of the mark" or a mark not exceeding a fixed size, or similar expressions refers to the longest dimension of that one character, for example, the width or the height of the single letter or the single number.

In some embodiments, the particles of the invention are marked with a combination of characters such as multiple letters and/or numbers that can be, for example, an identification or reference number. In other embodiments, a combination of characters can spell out the name of a product or a company. When combinations of alphanumeric characters are used as a mark on a tracer particle of the invention, the expression "maximum size of the marking" refers only to the maximum length or width of a single letter or number. As used herein, the expression "maximum size of the marking" and similar expressions does not refer to the full width of the multi-character designation such as in a name of a company or a multi-character identification number.

Is some embodiments, markings that are not larger than about 40 microns in any dimension (length or width) are generally used. Markings larger than about 40 microns in any dimension also find use with the invention. In other aspects, the invention provides smaller markings, for example, markings not larger than about 20 microns, 10 microns, 5 microns, 2 microns, or 500 nanometers (i.e., 0.5 microns). Smaller sizes such as not larger than about 200 nanometers or 100 nanometers are also available using the methods of the present invention.

As described herein, methods for producing the marked tracer particles can use traditional photolithography, as well as microcontact printing variations of photolithography. See EXAMPLES 1, 2 and 3. When those methods are used, markings as small as about 10 microns or about 20 microns can be produced.

In other embodiments, methods for producing the marked tracer particles utilize a reactive plasma etching procedure. See EXAMPLE 4. When using this procedure, distinguishing markings as small as 500 nanometers (0.5 microns), or smaller, can be produced.

A suitable size for the distinguishing marking on the surface of the particle may be dictated by the preferred size of the tracer particle, or vice versa. For example, if a tracer particle having a maximal dimension of about 100 microns is desired (or in a range of about 50 to 80 microns, or about 80 to 100 microns in size, or about 80 to about 150 microns in size), a distinguishing mark on the surface of that particle that is not more than about 0.5 microns to about 20 microns in its longest dimension would be preferable, so that the mark will fit on the particle and can be visualized on the particle. Where a particle having markings that are between about 0.5 microns and about 20 microns in size is desired, plasma etching methodology as provided herein can be used. In some embodiments, where a particle has markings that are about 0.5 microns in size, a particle size of not less than about 5 microns can be used.

If a tracer particle having a maximal dimension of about 400 microns is desired, a distinguishing mark on the surface of that particle that is not more than about 40 microns in its longest dimension, or between about 20 microns and 40 microns in size, would be preferable, for example, as can be produced using microcontact printing methodology as provided herein.

It is not intended that the invention be limited by the method used to produce the markings on the surface of the tracer particles. For example, in some aspects of the invention, microcontact printing methodology can be used to produce markings on tracer particles, where the microcontact printing is favorably used to produce markings generally larger than about 10 microns in size, for example, between about 10 microns and about 40 microns. In other aspects, plasma etching is used to produce the tracer particles and the markings on the particles.

The plasma etching methodology can be favorably used to produce markings on tracer particles, where the markings can be generally smaller than the marking produced by microcontact printing. For example, the plasma etching methodology can be favorably used to produce markings as small as 20 microns, or as small as 2.0 microns, or as small as 0.5 microns, or in other embodiments, smaller than 0.5 microns.

The markings used on the surface of the tracer particles is not limited in any regard. Although the use of alphanumeric characters are described herein, it is not intended that the invention be limited to the use of alphanumeric characters from the Romance languages alphabet and numbers as distinguishing markings. Any type of intentional mark can be used, such as any type of symbols, lines, arrows, geometric shapes, characters from any type of alphabet (including, e.g., Greek/Latin, Coptic, Cyrillic, Arabic, Hebrew, Chinese), mathematical operators (such as signs for addition, subtraction, multiplication or division), any type of mathematical notation such as mathematical relationships (equals, less then, greater than, equivalent to), symbols used in calculus and differential equations, currency symbols, musical notes, and even rudimentary representations of easily recognized objects (for example, an umbrella, a car, a person in stick figure representation, a soccer ball, a clock, a crescent moon), hieroglyphs, Braille and Morse Code. In some embodiments, the distinguishing markings on the tracer particles are non-biologically encoded, and/or are non-naturally occurring markings.

In still other embodiments, the distinguishing mark can be notation corresponding to any type of one-dimensional (linear) bar code or any type of two-dimensional bar code, also termed a matrix code. A variety of matrix codes can be used, for example, a QR code or microQR code, a "Data Matrix," "Aztec Code," a "MaxiCode," a "SPARQCode" or a PDF417 style code.

In some embodiments, custom tracer particles can be produced containing distinguishing markings or number/letter combinations that encode a product number, a source code, a manufacture date, an expiration date, a code indicating the identity of the bulk material, the name of a company or the name of a product or a product ingredient, or any other useful reference information.

In other embodiments, the tracer particles are provided in a combinatorial library. For example, a tracer particle library can be made from three different premade particles, for example, particles containing the characters "A," "B" and "C." From this library, a total of 7 different combinations can be made, which are ABC, AB, AC, BC, A alone, B alone and C alone. By adding one particle, or combining two or three particles in a bulk material, seven different unique identifiers can be quickly and cost effectively produced. In the authentication step, the person conducting the analysis will look for either one, two or three different particles in the manufactured item.

IV. Marked Articles

The present invention relates to tracer particles, e.g., magnetic tracer particles, with at least one identifying marking on at least one surface of the particle. Such particles have a wide variety of uses, including but not limited to security applications, tags for determining product authenticity, markers for quantifying bulk material mixing efficiency, measuring/detecting cross contamination and assaying the presence or absence of micro-ingredients in animal feeds or pet foods.

In some embodiments, marked articles, i.e., tagged products, are formed by the incorporation and dispersing of the tracer particles of the invention within a flowable dry bulk particulate material at the time of manufacture of the article. In some embodiments, the dry particulate material is in a powder form or in a granulated form. However, the invention finds use with any particulate material, including particulate materials that may fall outside the categories of powders and granulations. It is not intended that the invention be limited in this aspect. The present invention finds use with any particulate materials, including but not limited to particulate materials that are described as powders, agglomerates, granules, pellets or larger flowable bulk materials.

Powders are generally dry, bulk solids composed of very fine particles that may flow freely when shaken, tilted or poured. Granulars (granular materials) typically also have flow properties similar to powders, but are made up of larger (coarser) particles. Granulated forms are generally made of particles in the range of about 0.2 mm (200 microns) to 4.0 millimeters in size, while powders are generally made from particles that are smaller than granules. The distinctions between granulated and powdered materials vary by industry, and are arbitrary for the purposes of the present invention, and it is not intended that the invention be limited in any regard to this aspect.

In some embodiments, the marked articles remain in a flowable dry bulk particulate state, for example, in infant/baby powder formulas, or dry pharmaceutical formulations that will be dispensed in granular or powder form. In other embodiments, the marked articles have lost their flowable bulk particulate form where the tracer particles are ensconced in the solid article, such as in a solid pharmaceutical tablet. In that case, the tracer particles can be isolated and characterized by first grinding the solid form to produce a granulated or powdered material, from which the tracer particles can be isolated. It is preferable that the ground from of the solid be reduced to a particle size of 100 to 150 microns.

In many embodiments, the tracer particles are incorporated into human or animal consumables (i.e., ingested products) for the purpose of determining product authenticity downstream of the point of manufacture, including such products as human and animal oral pharmaceutical products, animal feed and animal feed premixes, and high value human consumables such as infant/baby formulas or other types of infant/baby foods.

In other embodiments, the tracer particles are incorporated into non-consumable products, such as plastics and explosive materials.

In embodiments where the tracer particles are incorporated into human or animal consumables, the tracer particles are manufactured using only materials that are suitable for human or animal consumption. For example, when the tracer particles are used to tag non-drug consumables, such as infant formula or other foods, the particles are produced using only materials that are generally regarded as safe (GRAS), as known and understood in the industry. The labeling of a material as GRAS is a designation from the United States Food and Drug Administration (USFDA) that a chemical or substance added to food is considered safe by experts.

If a tracer particle of the invention is produced using only GRAS materials, then these particles can be safely included within human consumables such as pharmaceuticals, nutritional products and food products.

Similar concerns with regard to counterfeiting activity and safe consumables also exist in the animal feed industry, including livestock feed and pet foods. Tracer particles of the invention can be manufactured using materials in compliance with those regulations, thereby making the tracer particles safe for inclusion in formula feeds for animals, poultry or fish. The feed industry has already permitted the use of some types of tracing particles in animal feeds to track features such as microminerals, salts and other drugs. See, for example, Murthy et al., "Evaluation of mixer efficiency test," *Indian J. Animal Nutr.*, v. 7(2):159 (1990); Calderon et. al., *Proceedings, Western Section, Amer. Soc. of Animal Science*, v.51:1 (2000) and Zinn, "A guide to feed mixing," *Research Updates and Reports*, Desert Research and Extension Center, Department of Animal Science, Univ. of California Davis (1999). For additional description of how tracer particles of the invention can be used in the animal feed industry, see also, for example, U.S. Pat. No. 6,406,725 and International Patent Application Publication No. WO2012/103476. In still other embodiments of the invention as used in the feed industry, whether or not an animal has consumed any marked product such as a feed ration or a medication, the snout of the animal can be examined for the presence or absence of the tracer particle.

One example of feed that can be tagged with a tracer particle of the invention is a formula feed for poultry, which contains primarily ground corn and soybean meal, with "macro-minerals" (such as calcium and phosphorous compounds), amino acids, "micro-minerals" (such as zinc and selenium), vitamins, drugs, enzymes, probiotics, mycotoxin binders and other ingredients. Formula feeds can contain hundreds of different ingredients depending upon the species fed and market prices for the ingredients. "Least cost" linear programming is commonly used to achieve the desired nutrient profile at the lowest cost. Formula feeds are a bulk flow particulate material, and can be tagged with a tracer particle by incorporating the particle into the feed. Alternatively, any one component of the formula feed can be tagged with a tracer particle of the invention, so that authenticity of that one component can be tested prior to addition of that component into the formula feed mix.

In other embodiments, whether or not a human or an animal has consumed any marked material containing the tracer particles of the invention can be determined by examining the fecal matter from that individual, where the fecal matter is assayed for the presence or absence of the tracer particles.

It is not intended that the invention be limited to the tagging of flowable dry bulk particulate material. The tracer particles of the invention can also be incorporated into liquid bulk materials, or flowable compositions that behave as liquids, such as suspensions, slurries, colloidal solutions and lipids such as oils. In these embodiments, the tracer particles tag the wet materials and can be used as authenticity markers. The ability to tag wet materials finds particular use in high-risk categories of wet materials, such as medicinal liquid gels, such as gel capsules (e.g., LiquiGels), medicinal liquid-filled capsules (e.g., LiquiCaps®), cough suppressants and expectorants, premixed liquid infant/baby formulas, or exceptionally high-value foods.

When lipids are used as a liquid bulk material (e.g., a liquid excipient), lipids that are in a liquid state at room temperature are generally preferred. Lipids is a term that includes, for example, oils, fats, shortenings, and waxes, and may be either solid or liquid at room temperature, depending on their structure and composition. Lipids consist of a diverse group of compounds that are generally soluble in organic solvents and generally insoluble in water. The term "oils" is usually used to refer to lipids that are liquids at room temperature, while the term "fats" is usually used to refer to lipids that are solids at normal room temperature.

When a flowable bulk material is used to form a marked product by the addition of tracer particles of the invention, it is not intended that the invention be limited by the nature of the bulk matter. The bulk matter can be matter of any type or composition, for example, dry particulate or granular, or liquid. Further, the bulk matter need not be entirely dry or entirely wet. Fat (lipid) compositions in particulate form find use with the invention as bulk material. Particulate compositions can contain all or some portion of liquid, for example, emulsifying agents, alcohols, or organic acids. Bulk flow particulate materials can comprise fats, proteinaceous solids (e.g., gelatin and sodium caseinate) or carbohydrate solids (starches and sugars), and all find use with the invention.

V. Marked Pharmaceutical Products

The present invention provides materials and methods for producing marked pharmaceutical products. The marked pharmaceutical products are formed by the incorporation of the tracer particles of the invention into the bulk phase during pharmaceutical manufacture. The marked pharmaceutical products can be human pharmaceuticals or animal pharmaceuticals.

As used herein, the terms "pharmaceutical," "pharmaceutical product," "medicinal product" or "medication" or similar terms refer generally to any manufactured product that is administered to a person or animal that is intended for use in the medical diagnosis, cure, treatment, or prevention of disease, or to restore, correct or modify any physiological functions. A pharmaceutical product can be intended for oral administration, or can be intended for any other type of administration, such as parenteral, inhalation, sublingual, topical, rectal or vaginal.

As used generally in the art, and herein consistent with that use, the term "drug" can refer either to a manufactured pharmaceutical product or medicinal product, or alternatively, only to the biologically active component that is contained in the pharmaceutical or medicinal product.

Oral medications generally contain a pharmacologically inactive "bulk material" (alternatively termed excipients, bulking agents, fillers or diluents) in addition to the active ingredient. The bulk material facilitates convenient and accurate allocation of the active ingredient and formation of a delivery vehicle, for example, a tablet or capsule. According to the present invention, tracer particles can be added to the excipient material at the time of drug manufacture, in parallel with the active ingredient. This process creates a tagged (or marked) pharmaceutical product that can then be tested for the presence or absence of the tracer particle at any point post-production. Presence of the tracer particle in the tested article would confirm an authentic drug product, and conversely, failure to detect the tracer particle, or insufficient number of tracer particles, would indicate a fraudulent product or product tampering.

In pharmaceutical formulations, a wide variety of dry excipients are known and used. For example, excipients can include any one or combinations of materials such as antiadherents (magnesium stearate), adherents, dry binders (cellulose, methyl cellulose, polyvinylpyrrolidone and polyethylene glycol; saccharides and their derivatives; disaccharides: sucrose, lactose; polysaccharides and their derivatives: starches, cellulose or modified cellulose such as microcrystalline cellulose and cellulose ethers such as hydroxypropyl cellulose (HPC); sugar alcohols such as xylitol, sorbitol or maltitol), protein fillers (gelatin), synthetic polymers (polyvinylpyrrolidone (PVP), polyethylene glycol (PEG)), coatings such as tablet coatings (e.g., a cellulose ether hydroxypropyl methylcellulose (HPMC) film coating, synthetic polymers, shellac, corn protein zein or other polysaccharides, and capsule coatings such as gelatin), enteric coatings (fatty acids, waxes, shellac, plastics, and plant fibers), disintegrants (e.g., crosslinked polymers: crosslinked polyvinylpyrrolidone (crospovidone), crosslinked sodium carboxymethyl cellulose (croscarmellose sodium)), modified starches, fillers/bulking agents/diluents (e.g., plant cellulose (pure plant filler), dibasic calcium phosphate, vegetable fats and oils, lactose, sucrose, glucose, mannitol, sorbitol, calcium carbonate, and magnesium stearate), flavorings, colorings, lubricants (talc or silica, and fats, e.g. vegetable stearin, magnesium stearate or stearic acid), glidants, sorbents, preservatives, and sweeteners.

In pharmaceutical formulations, liquid or otherwise wet excipients are also known and used. The tracer particles of the invention can be added to these liquid excipients, and used in a manner similar when added to a dry bulk material. For example, wet or liquid excipients can include any one or combinations of materials such as water, solubilisers (sorbitol, dextrose), sweeteners (propylene glycol-glycerine (glycerol)), water-miscible co-solvents (propylene glycol, glycerol, ethanol, low molecular weight PEGs), and water-immiscible co-solvents (e.g., emulsions/microemulsions using fractionated coconut oils).

In some embodiments, for example, in tablet-form pharmaceuticals, the tracer particles need not be incorporated into the bulk material that contains the active ingredient. In this case, the tracer particles can be incorporated into an outer protective coating that covers the tablet. During the manufacture process the outer protective coating is applied as a bulk material (typically starting as a liquid form), and the tracer particles are added to that coating bulk form prior to application onto the uncoated solid tablet. In this case, the presence or absence of the tracer particle is assayed to determine product authenticity no differently than if the particle has been incorporated into the bulk material in the interior of the tablet.

In the manufacture of pharmaceuticals, preferred materials are those materials that satisfy all food-grade standards and generally mix uniformly into the drug formulation (e.g., any added component must ideally be capable of mixing with the excipient material). Any component added to a pharmaceutical formulation must generally be safe, have no undue effect on the biological activity or efficacy of the active ingredient, have no undue effect on stability of the active ingredient or any other component of the formulation, and ideally must not interfere with any assay for the active ingredient(s), for example, a biochemical assay or an immunoassay.

The invention provides tracer particles that comply with these safety requirements. The materials used to manufacture such particles can for example include only FDA approved GRAS materials, such as FDA approved ferromagnetic materials, for example, iron, iron-nickel allows, gamma ferrioxide) and FDA approved polymer binders, for example, bleached dewaxed shellac, gelatin, derivatives of cellulose such as ethylcellulose, hydroxyethyl cellulose, hydroxypropyl cellulose, hydroxypropyl methyl cellulose, methyl cellulose; rosin resins such as gum rosins, tall oil rosins, wood rosins and hydrogenated resins. In some embodiments, the tracer particles are formed from materials that are intended to degrade or be metabolized after their ingestion.

VI. Use of Tracer Particles in Forensics

In some embodiments, the tracer particles of the invention find use in forensics applications. The inclusion of tracer particles in explosive materials can allow investigating authorities to identify the manufacturer of explosive bulk materials, and thereby provide investigative leads to the identification of the supplier of materials to make an explosive device, when or where an explosive device was made, or how explosive raw materials were acquired.

The tracer particles of the present invention find use in forensic applications, for example, by their incorporation into explosive materials. Such tracer particles can be produced to optimize their use in this type of application. For example, the tracer particles can be exceedingly small (e.g., not more than 100 microns in any dimension), or be larger in size. The tracer particles are detectable in the raw materials prior to ignition/detonation of the explosive material, but most ideally, tracer particles can be produced that will survive detonation of the explosive material. For example, particles made of pure iron or an iron alloy will serve this purpose.

The invention finds use in the tagging of powder/granular forms or liquid forms of explosives, or reagents for producing explosives. Such materials include, but are not limited to, trinitrotoluene (TNT), ammonium nitrate, urea nitrate, nitroglycerin, pentaerythritol tetranitrate (PENT), triacetone-triperoxide (TATP), and hexamethlene triperoxide diamine (HMTD).

VII. Methods for Tracer Particle Isolaton and Detection

The present invention provides methods for the isolation and visualization of the magnetic tracer particles. Magnetism has been shown to be a rapid, simple and effective means to isolate magnetic particles from either bulk particulate material or from a liquid phase, and is adapted for use in the present invention.

Generally, the magnetic material used in the particles can be the actual substrate of the particle, for example, particles of pure iron or an iron alloy, or the magnetic material can be a supplement that is added to a non-magnetic matrix that forms the physical structure of the particle. See, for example, U.S. Pat. No. 3,469,990; U.S. Pat. No. 4,029,820; U.S. Pat. No. 4,152,271; U.S. Pat. No. 4,188,408; and U.S. Pat. No. 4,654,165.

In some aspects, the present invention provides ferromagnetic tracer particles, where the particle is made of iron. In other aspects, the invention provides ferromagnetic tracer particles that comprise a polymer matrix into which is incorporated a ferromagnetic material, for example but not limited to, ground iron (powder or granular form). As a result, either of these types of particles is attracted to magnets (i.e., ceramic magnets, rare-earth magnets or electromagnets), yet will lose its magnetism in the absence of a magnetic field. Therefore, the tracer particles do not clump with each other and will mix uniformly into bulk material.

The invention also relates to methods for tracer particle collection and identification. Generally, the tracer particle needs to be in a flowable state where it can be isolated away from the bulk material within which it is contained. In some embodiments, the bulk material is in a freely flowable form, such as a powder or granular bulk material, or in a liquid bulk material or a liquid-like bulk material. In other embodiments, the material from which the tracer particles are being isolated is a solid that has lost its flowable bulk form, such as in a solid pharmaceutical tablet. In that case, the solid form is ground to form a granulated or powdered material, from which the tracer particles can be magnetically isolated.

The ferromagnetic tracer particles of the invention can be isolated from bulk material using any suitable magnetic separator or magnetic probe containing a ceramic or rare-earth magnet. For example, a laboratory magnetic separator such as the MicroTracer, Inc. Rotary Detector™, as described in Eisenberg, "The use of Microtracers™ F (colored uniformly sized iron particles) in coding the presence of coccidiostats in poultry feeds," *Zootechnica International*, Vol. 12, p. 46-50 (December 1998). Any magnetic separator instruments/apparatus for the isolation of magnetic particles from dry materials can also be used. For example, a mason jar kit can also be used, as described in U.S. Pat. No. 4,152,271.

Alternatively, magnetic probes or magnetic wands can be used to retrieve tracer particles that are suspended in a water slurry, or contained in any liquid phase, such as from true solutions, suspensions, colloidal solutions, or oils. When a magnetic wand is used to collect (isolate) the tracer particles, the wand is generally a hand held magnetic device comprising a housing with a magnet placed inside the housing. A handle is mounted to the housing to provide for convenient manipulation of the magnet inside the wand. The wand is exposed to the liquid, then removed, and the particles are collected from the housing of the wand.

Examples describing methodology for the isolation of magnetic particles are described, for example, in Eisenberg, "The use of Microtracers™ F (colored uniformly sized iron particles) in coding the presence of coccidiostats in poultry feeds," *Zootechnica International*, Vol. 12, p. 46 (December 1998); Eisenberg, "Microtracers™ F and their uses in assuring the quality of mixed formula feeds," Advances in Feed Technology, Vol. 7, p. 78 (1992); and Eisenberg, "Validating cross-contamination control," *Feed International*, 1 (2006).

Visualization of the tracer particles of the invention is generally by means of visual magnification of the magnetically isolated particles. The tracer particles of the invention are too small to be visualized without magnification. The means for visual magnification is not limiting. Minimal magnification, for example, on the order of about 40×, 60× or 100× is sufficient to view the tracer particles and the distinguishing markings on the surface of the tracer particles. This degree of magnification can be easily obtained with simple visible light microscopy, such as in stereoscopic microscopy (e.g., a dissecting style microscope) that uses incident (reflected) light illumination to view the surface of an object. A wide variety of such microscopes can be used, and in some embodiments, the magnifications provided by some portable and/or "pocket" microscopes is sufficient.

Optionally, field-of-view images from the light microscope can be captured by any light-sensitive means to generate a micrograph. Such means includes photographic film, and more modernly, CMOS and charge-coupled device (CCD) cameras for the capture of digital images. Purely digital microscopes and imaging equipment systems are also available where a CCD camera is used to visualize a sample, showing the resulting image directly on a computer screen without the need for eyepieces.

Figure 7:
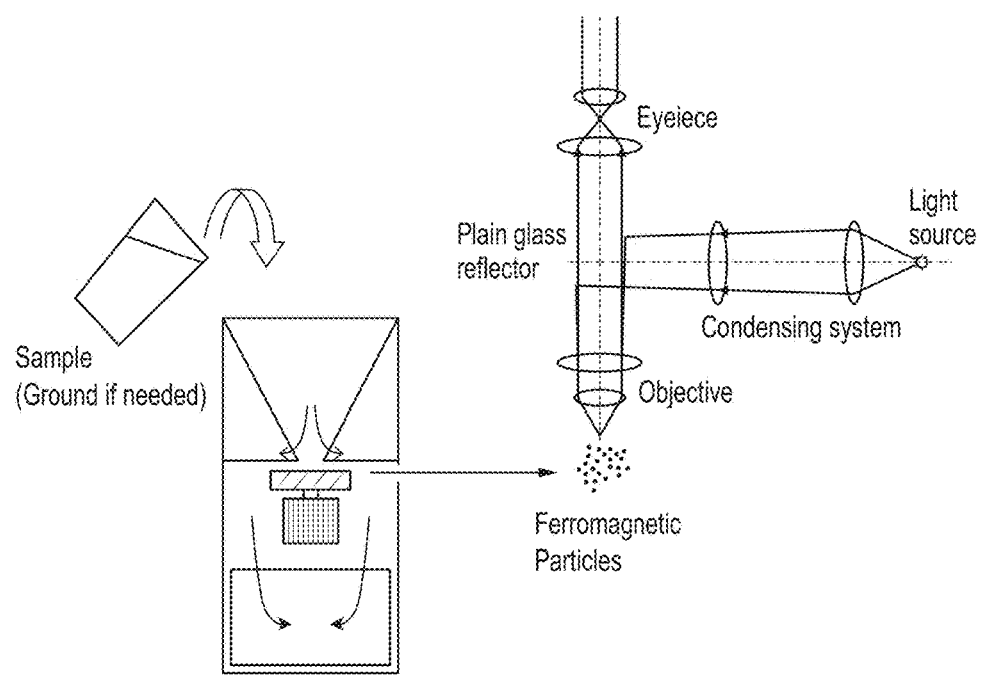
FIG. 7 provides a schematic depicting one method for the isolation and visualization of magnetic tracer particles of the invention.

FIG. 7 illustrates some aspects of isolating and detecting the ferromagnetic tracer particles of the invention. In this figure, a sample is first prepared for analysis. Samples should be in a particulate state, most preferably in a fine grained powder, or less preferably in a granular state. If a sample for analysis is a bulk solid (such as a tablet) or is in a particulate state that is too coarse, the sample must be ground to a finer particulate state.

The particulate samples for analysis are placed into a magnetic separator instrument, for example as shown in the figure, a MicroTracer, Inc. Rotary Detector™ magnetic separator, which provides easy separation of the particles based on their magnetic properties. Other magnetic isolation systems can also find use with the invention. In some embodiments, automated apparatus is not required, as simple, unsophisticated methods using a powder slurry (e.g., a powder suspended in water) and a simple magnet can also be effective at isolating the ferromagnetic tracer particles. Also shown in FIG. 7 is a schematic of a magnification device for viewing the ferromagnetic particles, e.g., a stereomicroscope (using incident light). The eyepiece, light source, plain glass reflector, condensing system, and the objective are indicated.

VIII. Tracer Particle Secondary Features

The tracer particles of the present invention comprising distinguishing markings can be produced containing optional secondary features that aid in detection or analysis of the particles. For example, the particles can be produced with a coating that aids in their visualization, or a visualization agent can be incorporated into the structure of the particles. These secondary visualization agents can create an additional detectable feature or contribute to combinatorial diversity from a single ferromagnetic particle.

For example, the particles of the invention can optionally comprise one or more conventional or fluorescent dyes or pigment, or thermochromic dyes, or any colorimetric compound. When these secondary materials, for example dyes, are used as coatings on a tracer particle, some of the dye or other coating material can be lost from the surface of the particle due to abrasion and diffusion in the bulk material; however, qualitative and quantitative particle recovery is unaffected. In animal feed applications, essential nutrients or drugs may themselves be used as identifiable coatings.

In some embodiments, the magnetic tracer particles are isolated from bulk material, but may still be difficult to detect and/or visualize. For example, when tracer particles are isolated from animal feeds, it may still be difficult to distinguish the tracer particle from "tramp iron" common to many types of animal feeds. In that case, it is advantageous for the tracer particles to contain some secondary feature to facilitate visualization. This can be easily accomplished by incorporating a chromogenic material, a chromophore, a fluorogenic material, a fluorophore, or thermochromic material into the tracer particle, or as a coating on the tracer particle. This will facilitate the visualization of the particles, for example, by inducing color development (as from a water soluble dye) or fluorescence, e.g., when viewed under UV wavelength light. Using this secondary feature, the tracer particle can be magnetically retrieved and confirmed (authenticated) either with or without viewing the distinguishing marking that is etched on the particle.

In some embodiments, when dyes are used to optionally coat the tracer particles, it is preferable that the dyes are certified/approved under the United States Federal Food, Drug, and Cosmetic Act (FD&C), thereby allowing the use of tracer particles of the invention in human and animal consumables. See, for example, U.S. Pat. No. 4,654,165. Some natural food colorings that can be used with the tracer particles of the invention are generally recognized as safe (GRAS) by the FDA and do not require FD&C certification.

Other supplemental features that can be used in conjunction with the tracer particles of the invention include tracer particles that comprise layers displaying different colors in the visible spectrum, or components that emit various spectral signatures when exposed to various excitation energy forms; see, for example, U.S. Pat. Nos. 6,647,649 and 7,038,766. Tracer particles of the invention can optionally include naturally occurring biological micromorphological structures that can be identified using microscopic examination; see, for example, U.S. Pat. Nos. 7,807,468 and 7,964,407. Optionally, the tracer particles can be produced having unique shapes or outlines that can serve as a secondary confirmation feature.

IX. Methods for Tracer Particle Manufacture Using Traditional Photolithography

The tracer particles of the invention will be of sufficient technical complexity such that the particles are not easily reproduced or mimicked by counterfeiters. This is accomplished by using micropatterning technology to produce particles that have microscale features that will be very difficult for unsophisticated counterfeiters to reproduce. One method used to produce particles having these features is photolithography with wet chemical etching.

In some embodiments, the process used to generate the tracer particles of the invention is traditional photolithography. In traditional photolithography, a metal substrate is etched with a defined pattern by use of a photomask and a light-sensitive photoresist layer. After light exposure, the photoresist layer is developed, and the resulting pattern is then chemically etched into the metallic substrate layer below the photoresist.

A) Preparation

The metallic material to be etched is typically in the form of a wafer or disk. Iron or steel foil is commonly used as a substrate, with a thickness between 10 and 100 microns. The disk is cleaned with an organic solvent, such as ethanol, to make sure that it is free from dust, dirt or residual oil. The cleaning can include heating, e.g., 100° C., to remove any residual moisture remaining on the disk surface. A liquid or gaseous "adhesion promoter" can optionally be applied to promote adhesion of the photoresist to the disk.

B) Photoresist Application

The disk is covered with photoresist by spin coating. First, a viscous, liquid solution of photoresist is dispensed onto the disk, and the disk is spun rapidly to produce a uniformly thick layer. The photoresist-coated disk is then baked to drive off excess photoresist solvent.

Resists are generally formulated with polymer loadings of 15 to 30 percent by weight with respect to the solvent content of the resist solution. The viscosity of the solution can be adjusted by varying the polymer to solvent ratio, thus allowing resists to be formulated for coating a variety of film thicknesses. In the present invention any of the numerous coating methods can be used to apply the resist. The most common are spin coating and dip coating.

A spin coating procedure is used in order to produce a precise, constant thickness of photo-resist across the sample. The speed of the spin coater between 1000 and 7000 RPM is recommended for approximately one minute. After starting rotation, a few drops of the photo-resist solution is applied onto the center of the substrate, centrifugal forces even spread the resist. Variants of this procedure are described throughout the literature.

Photo-resists systems consisting of a cresol-formaldehyde novolac resin and diazonaphtoquinone as a photosensitive dissolution inhibitor have received a considerable attention due to their high resolution, high thermal stability, and resistance to dry-etching conditions. Ito, "Functional Polymers for Microlithography: Nonamplified Imaging Systems", *In Desk Reference of Functional Polymers: Synthesis and Applications*, ed. by R. Arshady, ACS, N.Y. (1996). However, the invention is not limited in this aspect. Any suitable photoresist material can find use with the invention, including but not limited to poly(methyl methacrylate) (PMMA), poly(methyl glutarimide) (PMGI), phenol formaldehyde resin (DNQ/Novolac), and SU-8.

Soft baking of the photoresist layer after application to the disk makes the photo-resist more sensitive to UV-light by removing the solvent component of the photo-resist. A heating for 30-180 seconds at 70-130° C. is recommended for soft baking process. Too short of a prebake will prevent UV-light from reaching the photo-active component due to an excess of solvent remaining in the photo-resist. Overbaking the sample will increase the sensitivity to UV light and, in severe cases, may destroy the photo-active component and reduce the solubility of the photo-resist in the developer. Because the solvent is mostly removed, the thickness of the photo-resist will usually decrease by about 25% after soft baking.

C) Exposure and Developing

After application and drying, the photoresist is exposed to a defined specified pattern of light, typically in the ultraviolet spectrum. The exposure to light causes a chemical change that allows some of the photoresist to be removed by a subsequent "developer" rinse solution, called by analogy with photographic developer.

The light that reaches the photoresist layer is controlled by a photomask. In advance of the light exposure, a photomask containing opaque and transparent sections corresponding to the desired micropattern is manufactured. Photomasks are generally chrome coated glass lithographic templates designed to optically transfer patterns to wafers or other substrates in order to fabricate planar type devices. Basically, the pattern information is created in a drawing package and stored in a database, reformatted and transferred to a lithography tool, e.g., a laser writer, then printed in a layer of photoresist that is coated onto the photomask plate. The imaged pattern is next developed to form a template over the opaque chrome and then the chrome is etched away where the resist is clear. After the etch process is complete, the remaining photoresist is removed and the plate cleaned.

The finished photomask acts as a patterned light screen when positioned between a light source and the photoresist layer. After the photoresist layer is deposited, the photomask is applied onto the photoresist, followed by light exposure. The mask prevents light from reaching the photoresist in some areas, and allows light to pass in other areas. Exposure to light occurs through the mask with an optical reduction in the size of the image. A post-exposure heat treatment is performed immediately after light exposure and before developing. Maskless lithography projects a precise beam directly onto the photoresist layer on the disk without using a mask, but this technique is not widely used in commercial processes.

After the photomask is removed, the disk and the photoresist layer a subjected to the develop chemistry. This development solution removes the portions of the photoresist layer that have not been rendered permanent by either light exposure, or protection from the light exposure (depending on the particular photoresist chemistry that is used). The developer chemistry is delivered on a spinner, much like the photoresist. Historically, developers containing sodium hydroxide (NaOH) were originally used. Modernly, metal-ion-free developers such as tetramethylammonium hydroxide (TMAH) are commonly used.

Positive photoresist and negative photoresist protocols are available, according to the action of light and the photoresist chemistry that is used. In a negative working resist, the monomer or oligomer resist material is deposited on the metal surface in the form of a viscous liquid. It is then irradiated through the photomask and polymerization (cross-linking) takes place on the exposed area. The unirradiated liquid monomer is then washed away in a suitable solvent, and the exposed metal can be dissolved (completely or partially) in an etching bath. Finally, the remaining protective photoresist polymer layer is removed by chemical or mechanical means and the printed image is ready.

In a positive working resist, the monomer is first polymerized over the entire metal surface, then the protective polymer layer is irradiated through the photomask. In the areas that are irradiated through the mask, the polymer is degraded into smaller units and becomes soluble; it can then be removed by treatment with a suitable solvent and the etching bath will attack the exposed metal. A variation of this technique can be used for a preparation of integrated circuits one micron in size. The description presented herein uses a negative photoresist, but a positive photoresist can also be used.

Typically, the substrate of iron or steel foil covered with a layer of photo-resist is exposed to UV-light, using the photomask to create both exposed and unexposed portion of resist. In present invention, a UV-lamp with a maximum of emission at 365 nm was used on this step. The time of exposure is determined largely by the energy of light (usually between 150 and 500 $mj/cm^2$) and can vary from several minutes to several hours depending on distance from light source to substrate. It is important to keep the mask as close to the sample as possible in order to reduce dispersion and diffraction of light caused by the gap between the mask and the sample.

The solvents used to develop novolac photo-resists after light exposure are generally aqueous alkaline solutions. The earliest developers used for novolac resists were metal hydroxide solutions, such as dilute KOH or NaOH. In cases, when the substrate is more sensitive to metal contamination, for instance for semiconductor industry, metal containing developers are replaced by organic non-metal developers such as solutions of tetramethyl ammonium hydroxide in water.

The dissolution of novolac resins in aqueous developers is not a simple polymer dissolution process. In order for the novolac resin to dissolve into the aqueous solution, hydroxide ions from the solution must first deprotonate some of the phenolic sites on the novolac chain. In this way, dissolution of novolac into aqueous developers is more similar to an etching process, such as metal dissolving in an acidic solution.

In present invention an aqueous solution of sodium hydroxide and/or sodium silicate with concentrations from 0.1% to 10% are used in the developer step. Between 20 and 300 seconds of developer treatment is recommended depending on the concentration and ambient temperature.

After developing, hard-baking the sample at temperature around 110° C. will strengthen the remaining photo-resist and improve adhesion between photo-resist and the substrate, so that the photo-resist will not be removed by the etching. In present invention, the hard-baking at temperature between 80° C. and 125° C. for a period of time between 30 and 180 seconds is recommended.

D) Wet Etching

In the etching step, a wet chemical agent removes the uppermost layer of the metal substrate in the areas of disk that are no longer protected by photoresist. A variety of wet chemical etching reagents find use with the invention, for example but not limited to, ferric chloride or ferric sulfate, and mixtures of several components, for example phosphoric acid, nitric acid, acetic acid, and water (4:4:1:1). The invention is not limited to any particular formulation for wet etching.

The etching intensity is dependent upon the temperature of the reaction, and the concentration of the etching. Conditions must be carefully selected to avoid the etching mixture attacking the photo-resist, especially at higher temperatures. See, U.S. Pat. No. 6,362,083.

During the chemical etching, the metal layer to be patterned is inevitably subjected to what is called "side etching" by an amount dependent upon the length of chemical etching, resulting in the patterned metal layer becoming smaller than the pattern of the mask layer by the amount of side etching. The amount of side etching depends upon the temperature, the flow rate, and other conditions of the etchant used; therefore, it is very difficult to predict the amount of side etching, and etching conditions may need to be empirically determined.

In some methods of the invention, the aqueous solution of ferric sulfate with a concentration between 5% and 40% is selected due to the fact that it is on the list of the FDA approved compounds and provides the fast etching effect. An approximate etch time between 2 and 200 seconds is recommended, depending on the concentration of etching agent and the ambient temperature, which may vary from 15° C. and 60° C.

E) Photoresist Removal

After the photoresist layer is no longer needed, it must be removed from the substrate. This usually requires a liquid "resist stripper", which chemically alters the resist so that it no longer adheres to the substrate. Alternatively, photoresist may be removed by a plasma containing oxygen, which oxidizes it. This process is called ashing, and resembles dry etching.

Figure 1B:
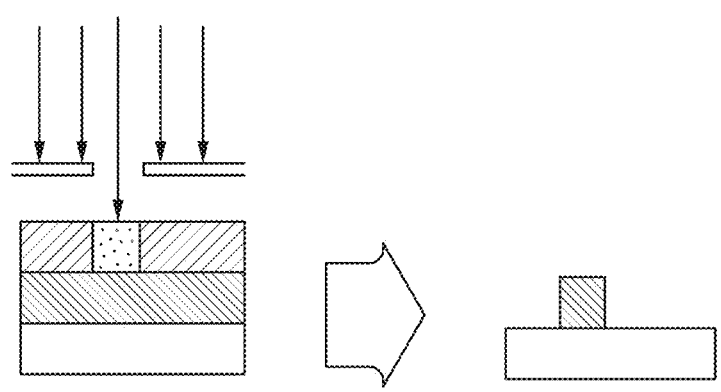

This traditional photolithography procedure is shown generally in FIGS. 1A and 1B. FIG. 1A illustrates a positive working photoresist. In that figure, a metal substrate (s), for example iron foil, is deposited on an optional insulator base (b). This metal substrate (s) is covered by an overlying photoresist layer (r). Irradiation of the resist through a photomask (m) results in photo-induced polymer destruction in areas of the photoresist layer that are exposed to the incident irradiation. This is followed by the developing rinse to remove the irradiated photoresist material and subsequent wet etching of the exposed metal substrate, to produce the final etched product.

FIG. 1B illustrates a negative working photoresist. In that figure, a metal substrate (s) is optionally deposited on an optional insulator base (b). This metal substrate (s) is covered by an overlying photoresist layer (r). Irradiation of the resist through a photomask (m) results in photo-induced crosslinking in areas of the photoresist layer that are exposed to the incident irradiation. This is followed by the developing rinse to remove the non-irradiated photoresist material and subsequent wet etching of the metal substrate surfaces that are revealed by removal of the non-crosslinked photoresist material, to produce the final etched product.

To produce the tracer particles of the invention, the engraved disk containing many images of the distinguishing mark is disintegrated into fragments of any desired size or size range, where each particle or nearly every particle contains at least one copy of the distinguishing mark.

X. Methods for Tracer Particle Manufacture Using Microcontact Printing

In one aspect of the invention, a microcontact printing procedure is used to produce distinguishing markings on the surface of the tracer particles. Microcontact printing initially uses the steps of traditional photolithography to first produce an etched "master" plate, which can be manufactured from metals such as iron or steel, or can be manufactured from silicone, where the master plate contains reiterations of the desired micrometer-scale or nanometer-scale patterning. That master plate is then used to form a reusable elastomeric stamp containing an inverted image of the desired microengraved pattern. The stamp is then used to generate many copies of the micropattern onto either a metallic substrate or a polymer substrate. Microcontact printing may incorporate traditional photolithography for making the master plate form, which can be a silicone master plate or a metal-based master plate. Because microcontact printing incorporates elastomeric materials, it is sometimes termed a modified version of soft lithography.

The original process of microcontact printing was proposed by Kumar and Whitesides in 1993. Kumar and Whitesides, *Appl. Phys. Lett.*, v.63, p. 2002 (1993). Modernly, technical improvements of the basic protocol have been made, including reducing stamp swelling during the "inking" process by using a "stamp pad" method, and the use of elastomer soaked in ink to localize the inking to the stamp corrugations. See, e.g., Quist et al., Anal. Bioanal. Chem., v.381, 591 (2005) and Libioulle et al., Langmuir, v.15, 300 (1999).

The disclosure herein described the use of elastomeric polydimethylsiloxane (PDMS) to form the stamp that is cast from the master plate. PDMS is commonly used to produce microcontact printing stamps because the product is optically clear, inert, non-toxic and non-flammable. However, it is not intended that the invention be limited to the use of PDMS to form a stamp, as other materials to form contract printing stamps are known to one of skill in the art, and can be selected in view of the intended use of the stamp.

In microcontact printing, the stamp thus produced from the master (in combination with a suitable ink) can be used in two different etching protocols. First, the stamp can be used to chemically etch a metal substrate, such as an iron foil. In that case, the ink that is used is an acid, such as hydrochloric acid (HCl) based solutions. Although the use of iron foil is described herein, it is not intended that the invention be limited to the use of iron foil, as other magnetic metals and metal alloys can also be used as substrate materials to generate the tracer particles of the invention, for example but not limited to iron-nickel and iron-cobalt, all of which find use with the invention. Similarly, other acid-based etch solutions can be used to etch the metal substrate, including but not limited to nitric acid, phosphoric acid, acetic acid, and mixtures thereof.

In a second methodology, the stamp can alternatively be used to chemically etch an organic polymer layer that contains iron or other ferromagnetic additive. As used herein, the expression "polymers finding use with the invention" or similar constructions refer to polymer binders, where polymerization or crosslinking of the polymer can provide a cohesive matrix from which tracer particles can be formed, and further, where the matrix is sufficiently dense to sequester or bind additional components that are present at the time of formation (i.e., at the time of polymerization or crosslinking). For example, polymers that can sequester a magnetic powder additive can be used to form the tracer particles of the invention.

When an organic polymer layer is used in the microcontact printing process, the ink that is used is an organic solvent like ethanol, which partly dissolves (swells) the polymer in the areas of the polymer that come into contact with the stamp. Although the use of ETHOCEL™ ethylcellulose is described herein as a polymer substrate, it is not intended that the invention be limited to the use of that polymer, as a wide range of other polymer materials are known to one of skill in the art and can be used with the invention, and can be optimally selected in view of the intended use of the tracer particles to be produced. For example, polymers (i.e., polymer binders) can be FDA approved polymer binders, for example but not limited to, shellac, gelatin, derivatives of cellulose such as ethylcellulose, hydroxyethyl cellulose, hydroxypropyl cellulose, hydroxypropyl methyl cellulose, methyl cellulose; rosin resins such as gum rosins, tall oil rosins, wood rosins and hydrogenated resins. Similarly, it is not intended that the invention be limited to the use ethanol as the etching material.

Figure 2:
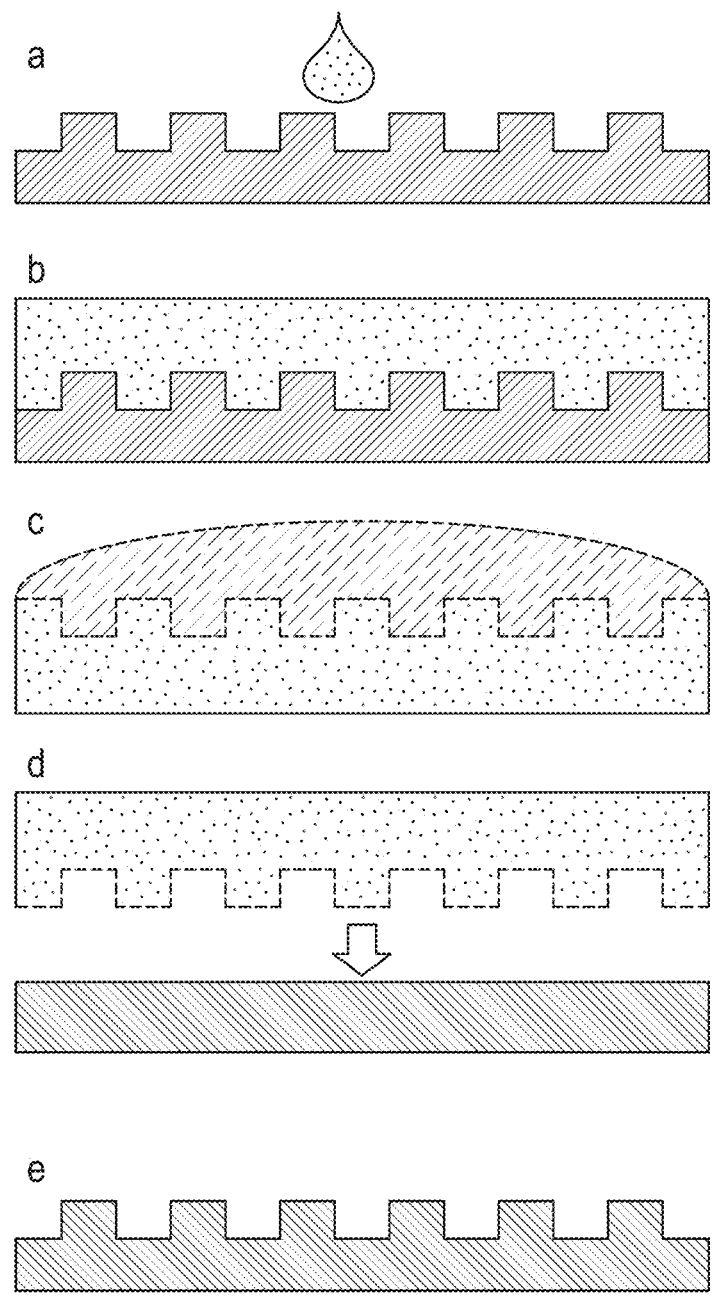
FIG. 2 provides a schematic depicting the theory of microcontact printing.

FIG. 2 shows a schematic representation of formation of a stamp and subsequent substrate etching in microcontact printing. An elastomeric material such as polydimethylsiloxane (PDMS) is applied to a master design template (step A) and allowed to cure (step B), thereby forming a removable stamp. After peeling the stamp away from the master, ink is applied to the stamp (step C). The ink is then transferred to a substrate by placing the ink-containing stamp into contact with the substrate (step D), i.e., stamping the substrate. After removal of the stamp, the desired micropattern is etched into the underlying substrate by the etching action of the ink (step E). In the case where the substrate is a metal, an acid-based ink can be used. In the case where the substrate is a polymer, such as a plastic, an organic polymer, or a food-grade polymer, an organic solvent-based ink can be used.

The microcontact printing process is clearly contrasted with traditional photolithography. In traditional photolithography, there is no intermediate stamp step, and the etching substrate is always a metallic substrate. Further, in traditional photolithography, the photoresist layer is applied directly to the substrate material that will produce the end product. In contrast, in microcontact printing, a photoresist process is only used in the construction of the master plate, and a photoresist is not used in production of the etched final product.

XI. Methods for Tracer Particle Manufacture Using Plasma Etching

The present invention provides methods for producing the magnetic tracer particles of the invention, where the methods utilize reactive plasma etching to produce the distinguishing markings on the surface of the tracer particles, as well as generating particles of predetermined defined sizes, and where the particles are separated from each other. This methodology can incorporate photolithography as one or more intermediate steps during preparation of the tracer particles.

Plasma etching generally follows the strategy of photolithography, with the important distinction of the etching process is delivered. Traditional photolithography uses wet chemical etching, where the process that removes either the metal or polymer substrate material is in a liquid phase. In contrast, the plasma etching process is a dry chemical etching, where the etching reagents are components of a reactive gas or plasma, and where the etching reaction consumes the substrate material by generating only volatile etching byproducts. Plasma etching includes techniques such as physical sputtering, ion beam milling and reactive ion etching.

Like wet chemical etching, dry etching also follows the resist photomask patterns on a wafer or disk, i.e., the process only etches away materials that are not covered by mask material (and are therefore exposed to the etching species), while leaving areas protected and covered by the photomask almost (but not perfectly) intact. These masks are deposited on the wafer by an earlier wafer fabrication step, consistent with traditional photolithography.

Plasma dry etching consists essentially of the following steps: (1) generation of reactive species in a plasma; (2) transport of these species to the surface of the material being etched; (3) interaction of these species with the surface; (4) occurrence of interactions between the species and the material being etched, forming volatile byproducts; (5) transport of the byproducts from the surface; and (6) transport of the desorbed byproducts into the bulk of the gas. Plasma etching can be used to produce patterned substrates (i.e., the tracer particles of the invention) that are either metallic, such as iron foil, or comprise a polymer, such as an organic polymer, where the polymer further includes iron or another magnetic additive.

As used herein, plasma etching is used to selectively remove material from a polymer stack. As used herein, the plasma etching step is always preceded by a traditional photolithography step. The plasma etching process of the invention can produce distinguishing markings having any desired dimensions, although most typically, the plasma etching methods are capable of producing markings on tracer particles that are smaller (i.e., have higher resolution) than the markings produced by microcontact printing methods of the invention. In some embodiments, the markings, for example alphanumeric characters, on the tracer particles that are produced by plasma etching are generally in the range of 2 microns to 20 microns in height. However, smaller characters, such as characters as small as 0.5 microns (500 nanometers), 100 nanometers, 65 nanometers or 50 nanometers are also producible with the plasma etching methods of the invention. Distinguishing markings larger than about 20 microns on the surface of tracer particles can also be produced by the plasma etching methods of the invention.

Figure 3:
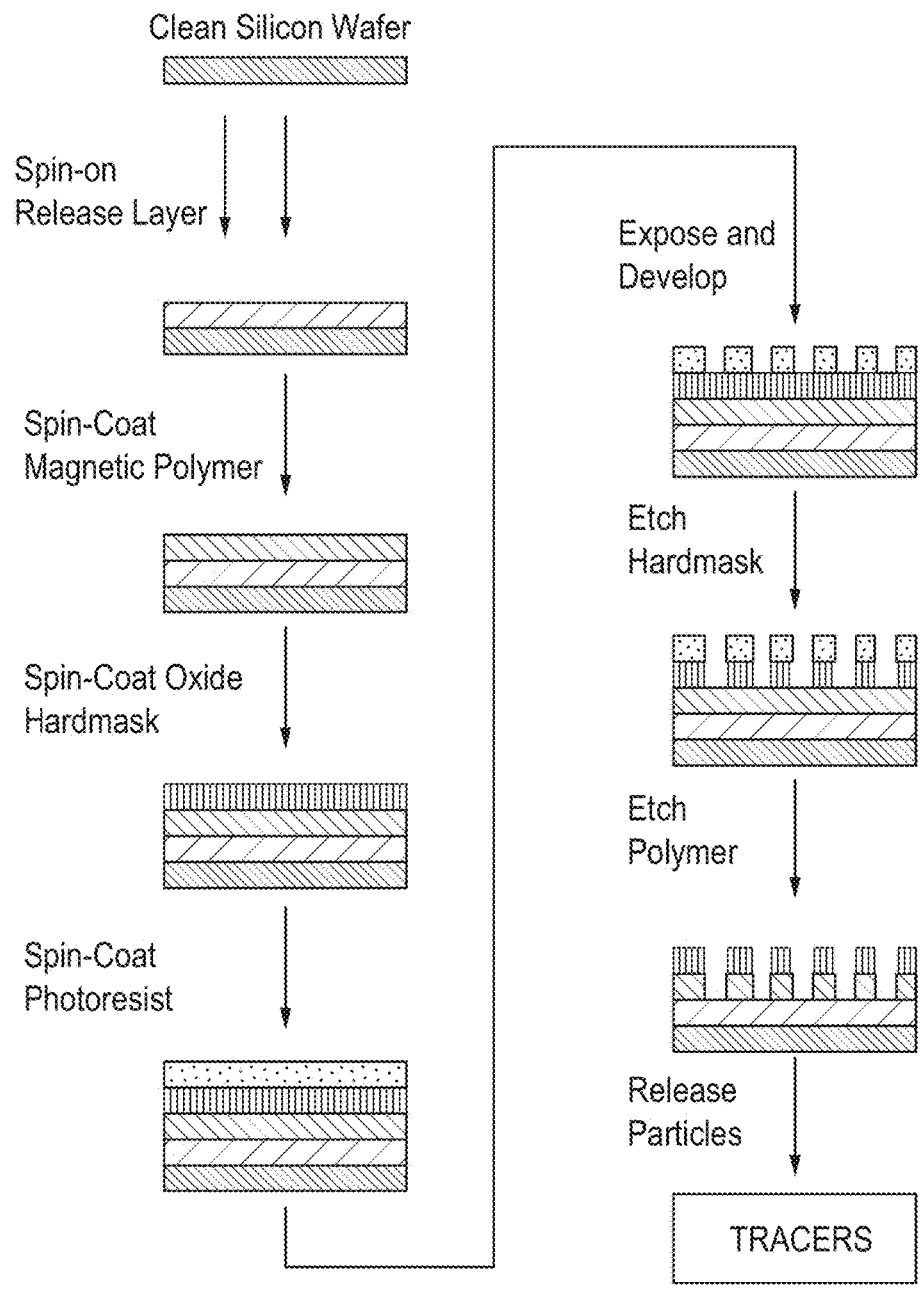
FIG. 3 provides a schematic depicting a method for the production of tracer particles of the invention using a plasma etching technique.

A schematic showing the general methodology for plasma etching to generate tracer particles of the invention is shown in FIG. 3. This process as shown in FIG. 3 is analogous to the plasma etch process that has broad application in the engineering of microelectronics in the semiconductor industry. For example, plasma etching is used to produce metallic connections between electronic components (such as resistors, capacitors and integrated circuits). This is accomplished by the selective etching of an insulating silicon oxide layer, followed by filling the gaps in the silicon oxide with a metal such as copper. The silicon oxide layer is protected by a resist, which is a polymer, deposited in such a way that it protects selected portions of the silicon oxide during exposure to a reactive plasma. The lines created when the silicon oxide is etched are later filled with metal and become the basis for creating circuits. See, e.g., U.S. Pat. No. 6,140,226, and Suppan, *Chemistry and Light*, Springer Press, The Royal Society of Chemistry, Cambridge, UK (1994).

The plasma etching process generally starts similarly to traditional photolithography, where materials are deposited as layers onto the surface of a substrate to be etched, followed by light exposure, photolithography, and finally the dry plasma etching to selectively remove material.

A) Deposition of a Silicon Oxide Liftoff Layer

The first step is to grow or deposit a layer of silicon oxide on a clean wafer. The purpose of this layer of silicon oxide is to act as a liftoff layer when the etching process is complete and the tracer particles can be conveniently released from the wafer. This layer serves to reduce the risk of stiction when removing the polymer particles from the wafer at the end of the process. This step may be considered optional, though employing it typically increases the breadth of the process window.

There are many methods of depositing silicon oxide onto a wafer, including thermal oxidation of silicon, plasma oxidation of silicon, deposition via PECVD (Plasma Enhanced Chemical Vapor Deposition) and application of a spin-on oxide. For this process, the preferred method is application of a spin-on oxide (Holmes et al., Appl. Opt., v.32, p. 4916 (1993)), although any suitable method finds use with the invention.

B) Application of the Magnetic Polymer Layer

Spin-coating is a commonly used method of applying a soluble material to a flat surface. Typically, a homogeneous solution of a polymer is prepared, and a few drops of the solution are placed at the center of a silicon wafer. The wafer is then spun at a predetermined speed until centrifugal force has removed the excess solution from the wafer. Spin coating was selected as the preferred method for coating the wafer with a magnetically active polymer substrate, in view of the wide availability of spin-coating equipment and reagents, and the well documented methods for spin coating taking into account material viscosity, density, solvent characteristics and layer characteristics.

C) Application of a Dielectric Hardmask

After the magnetically active polymer layer has been added to the wafer, a dielectric hardmask is deposited. The dielectric hardmask has two important functions. First, it separates the FDA-approved polymer from the photoresist that will later be used in patterning of the wafer, and second, it generates a chemically orthogonal system for etching. Various dielectric materials can be used, and the dielectric can be deposited in a variety of ways, all of which find use with the invention. The simplest material to use is silicon oxide and the simplest method of deposition is spin-coating from a spin-on-oxide.

Use of a dielectric hardmask is optional; the material can be manufactured without this step, albeit in a more complex and error-prone manner. It is important to note that the density of the dielectric layer is less important in this application than in typical semiconductor electronic applications. Even a dielectric layer that is not dense and that contains pinholes or other flaws can be used for this application.

D) Application of Photoresist

A wide variety of photoresists are known to one of skill in the art, any of which can be used with the invention. In one embodiment, the industry standard SU-8. Lorenz et al., J. Micromech. Microeng., v.7, p. 121 (1997). Photoresist material is sensitive to light in defined wavelengths, depending on the material that is used. Because SU-8 is photosensitive, all manipulations that involve this material must take place in a room illuminated with light in the yellow portion of the visible spectrum.

E) Photolithography

In order to prepare the wafer for etching, the photoresist must first be selectively exposed to patterned light through a photomask. Light of appropriate wavelength is passed through the mask to selectively expose portions of photoresist. After exposure, the photoresist is rinsed with a developer and baked.

F) Etching of the Dielectric Hardmask

Once photolithography is complete, the oxide hardmask and the magnetic substrate layer can then be etched. Both etching steps take place in a plasma etch tool. Most common plasma etch tools use a 13.56 MHz capacitively coupled plasma, though tools which use 2 MHz, 60 MHz, 120 MHz, 2.4 GHz or any other frequency of RF can also be used. The invention is not limited in this aspect.

The dielectric hardmask is etched first. In this step, the dielectric (i.e. silicon oxide) is the target material and the photoresist is the mask. Selectivity of approximately 1:1 to 3:1 is expected. A wide variety of fluorine-based plasmas can be used to etch silicon oxide; in some embodiments, a perfluoromethane ($CF_4$)/argon system is used because of its simplicity and ease of characterization. If an increased etch rate is desired, a small amount of oxygen or nitrogen can be added to the gas mixture.

G) Etching of the Magnetic Polymer Substrate

Once the oxide hardmask has been etched, the magnetic polymer is then be etched. In this step, the oxide hardmask is the mask and the magnetic polymer is the target layer. Selectivity of over 10:1 is expected. Several different gas mixtures can be used to etch organic polymers; in some embodiments, oxygen or a mixture of oxygen and argon are used to perform the main etch. If the material etches too quickly with this plasma, or if the etch is too isotropic, carbonyl sulfide can be added to slow the process and limit etching in the horizontal direction. A mixture of hydrogen and nitrogen (or just a short treatment of additional oxygen) can be used to clean the edges of the polymer after carbonyl sulfide has been applied. Nitrogen can also be added to the oxygen main etch if this process needs to be slowed.

This plasma etching process produces the engraving that adds the distinguishing marks to the polymer substrate, as well as cutting clear through the full polymer depth in defined patterns in order to separate the individual tracer particles from each other.

In other embodiments, reactive plasma etching is used to produce a distinguishing mark without etching completely through the magnetic polymer substrate layer, and in that embodiment, the polymer material remains in a sheet at the end of the etching process. In those methods, the tracer particles are generated by grinding the sheet and size sorting the resulting particles, as described herein. In still other embodiments, the plasma etching can be used to etch completely through the magnetic layer without producing a distinguishing mark.

H) Release of Magnetic Polymer Particles

Once the polymer substrate etching step is complete, the marked tracer particles of the invention have been produced. The only remaining step is to release and collect those particles from the silicon wafer support. To accomplish this, a wet etch can be used to dissolve the remaining silicon oxide hardmask and the oxide release layer. This releasing process should take place in a vessel of a wet etch solution such as $NH_4F/H_2O$ or $KOH/H_2O$.

To collect the particles, a strong magnet should be fitted with a plastic bag, then placed into the solution above the wafer. Once the hardmask and release layer have been removed, the particles can float free of the wafer and to the magnet. After the tracer particles have been collected, they should be rinsed in deionized water or another appropriate solvent and dried.

EXAMPLES

The following examples are offered to illustrate, but not limit, the claimed invention. It is understood that various modifications of minor nature or substitutions with substantially similar reagents or components will be recognizable to persons skilled in the art, and these modifications or substitutions are intended to be included within the spirit and purview of this application and within the scope of the claimed invention.

Example 1

Protocol for the Production of Tracer Particles Using Traditional Photolithography This example describes a method that was used to produce tracer particles using traditional photolithography and wet etching.

A) Preparation

The stainless steel foil Blue Tempered Shum Stock (Spring Steel C-1095 with a thickness of 0.002 inch (51 micron); Lyon Industries) was cleaned with ethanol, to make sure that it is free from dust, dirt or residual oil. The washed foil was subjected to baking at 100° C. for 4 hrs to ensure that any residual water on the sample evaporates out.

B) Photoresist Application

Novolac resin DNQ-novolac was dissolved in PGMEA (propyleneglycol methyl ether acetate) at a concentration 15% containing diazonaphthoquinone (DNQ) to form the photoresist material. Spin coating was used to produce a constant thickness of photo-resist across the steel foil substrate at a speed of about 1200 RPM for approximately 1 minute. After starting rotation, a few drops of the photoresist solution is applied onto the center of the substrate, and centrifugal forces evenly spread the resist. Soft baking to make the photo-resist more sensitive to UV-light by removing the solvent component of the photo-resist was performed by heating for 40 seconds at a temperature of 90° C.

C) Exposure and Developing

The stainless steel foil substrate covered with a layer of photo-resist was exposed to UV-light, using a photomask to create both exposed and unexposed portions of resist. A UV-lamp with a maximum emission at 365 nm (Black Light, Model ZB-100F; Magnaflux, Inc.) with an energy of light approximately 150 mj/cm$^2$) was applied for 6 hours, with the mask as close to the sample as possible in order to reduce dispersion and diffraction of light caused by the gap between the mask and the sample.

The developing novolac photo-resist was performed using 10% sodium hydroxide solution in deionized water for approximately 60-80 seconds. The sample was then hard-baked at a temperature of about 110° C. for 180 seconds in order to strengthening the remaining photo-resist and improve adhesion between the photo-resist and the substrate.

D) Wet Etching

Etching was conducted using an aqueous solution of ferric sulfate at a concentration of about 20%, with an exposure time of about 150 seconds at room temperature or alternatively for 80 seconds at 40° C.

E) Photoresist Removal

The residual layer of photo-resist was removed from the stainless steel foil substrate by treating with cyclohexanone at 45-50° C. for 10 minutes, followed by treatment with acetone for 10 minutes at ambient temperature, followed by a final rinse with ethanol and dried at ambient temperature.

Figure 4:
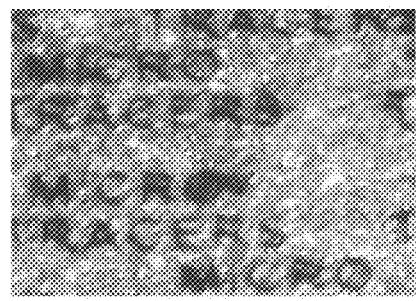
FIG. 4 provides a photomicrograph of an etched iron sheet that was produced using traditional direct photolithography.

FIG. 4 shows an photomicrograph of the intact iron foil at magnification of 60×. The height of the letters in "MICRO TRACERS" is approximately 40 microns.

E) Grinding

To produce tracer particles, the engraved foil was disintegrated into fragments using a coffee grinder, then consecutively sifted through two screens, one with size 40 mesh and other with size +60 mesh, thereby producing particles having a size range of approximately 250 microns to approximately 420 microns.

Example 2

Protocol for the Production of Polymer Tracer Particles Using Microcontact Printing This example describes a method for producing polymer-based tracer particles using microcontact printing, that is, by first producing a master template, from which is formed a stamp that is then used to image a polymer substrate that will form the tracer particles. Photolithography principles are used in the construction of the master plate.

A) Producing a Silicone Master Plate Traditional photolithography with a laser-produced photomask were used to generate a silicone master plate containing repeating patterns of the microetched mark, in this case, the word "MICROTRACERS."

B) Producing a PDMS Stamp

To make a PDMS stamp, the silicone master form with the micrometer-scale pattern of the work "MICROTRACERS" was used as a template. A mixture of liquid polydimethylsiloxane and SYLGARD® 184 silicone elastomer curing agent (Dow Corning), in a ratio of 10:1 was prepared, and degassed under vacuum for 20 to 30 minutes. The resulting solution was poured over the silicone master in a plastic petri dish.

The PDMS mixture was left in contact with the master pattern to cure for two hours at 65° C. At the end of that time, the resulting elastomeric mold is carefully peeled apart from the master form. This resulting flexible stamp produced a raised relief of the desired micropatterning image.

C) Preparing an ETHOCEL™ Polymer Film Containing Iron Powder

Titanium dioxide ($TiO_2$) powder (2.0 grams, pre-sifted) was dispersed in ethanol (52 ml) by magnetically stirring at room temperature for 15 min. The prepared dispersion was strained through a screen (#140 mesh size) to remove large $TiO_2$ particles. After returning to the magnetic heated stir plate, the dispersion was stirred and heated to 40 to 50° C.

Next, 6.0 g of ETHOCEL™ ethylcellulose polymer (Dow Chemical Company) was added to the dispersion, taking care to avoid agitating the dispersion or forming any clumps. After all of the ETHOCEL™ is dissolved, 19.0 g of the prepared solution was transferred to a beaker. While continuously stirring, electrolytic iron powder (5% by weight, powder size below 325 mesh) was added.

The uniform dispersion was added to a 100 mm diameter disposable Petri dish and place into vacuum chamber. Air bubbles were removed by subjecting the polymer solution to a low vacuum. Any remaining solvent was allow to evaporate in a refrigerator (5 to 8° C.) for 48 hours.

D) Stamping the ETHOCEL™ Film Substrate

An additional suspension of $TiO_2$ (0.5 g) and ethanol (10 mL) was prepared by vigorously stirring components for 15 minutes. The surface of the ETHOCEL™ ethylcellulose polymer film was moisturized with the new suspension and dried at room temperature. Before stamping, the PDMS stamp was moisturized with ethanol. The ETHOCEL™ film was stamped by placing the PDMS stamp into contact with the surface of the film using a force of about 1.5 to 2 kg/cm$^2$ of pressure for 15 minutes. The value of force applied was calculated by determining the weight of the stamping device (4.5 to 6 kg) divided by the surface area of the stamp (3 cm$^2$).

This stamping with ethanol partially dissolved (swelled) the polymer in the area of contact. The polymer film was then thermo-treat (i.e. ironed) between two metal sheets, then the stamping procedure was repeated on the opposite side of the polymer film.

E) ETHOCEL™ Film Grinding to Produce Particles

The printed areas of ETHOCEL™ polymer film were cut out and ground using a hand-held coffee bean grinder. The film was ground to a powder-like consistency. That powder was then consecutively sifted through 40 and 70 mesh-size screens, in that order, thereby generating a population of ETHOCEL™ film fragments ranging in size between about 210 and 420 microns.

Figure 6:
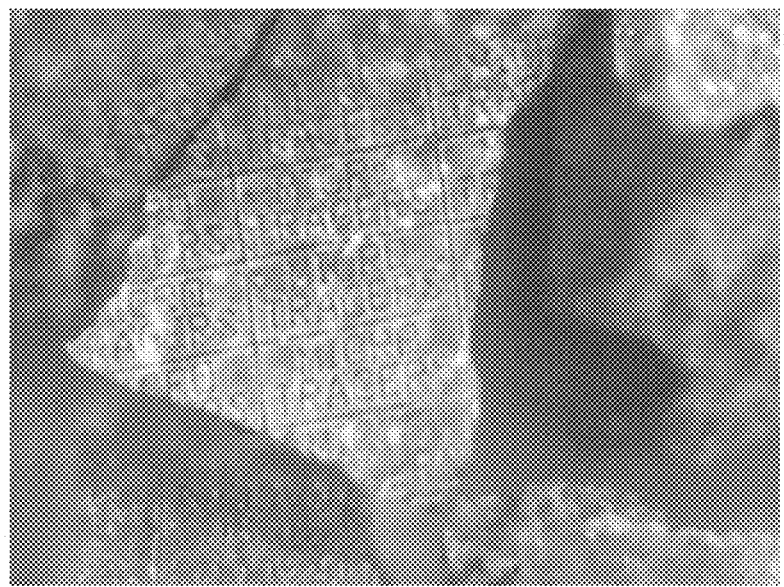
FIG. 6 provides a photomicrograph of iron-containing ETHOCEL™ tracer particles that were produced using microcontact printing.

The resulting magnetic particles were observed under a conventional OLYMPUS® CH2 Series optical microscope with magnification of 60×. A field of view was captured in the photomicrograph shown in FIG. 6. The height of the letters forming "MICROTRACERS" is approximately 40 microns.

Example 3

Protocol for the Production of Metal Tracer Particles Using Microcontact Printing This example describes a method for producing iron tracer particles using microcontact printing, that is, by first producing a master template, from which is formed a stamp that is then used to image an iron foil substrate that will form the tracer particles. Photolithography principles are used in the construction of the master plate.

A silicone master plate and a corresponding flexible PDMS stamp were produced as described above in EXAMPLE 2. In this case, the silicone master plate and PDMS stamp contained the test symbols "ABC".

After the PDMS stamp was created, it was coated with a protective "ink" comprising a light wax such as petroleum, paraffin or bees wax at a concentration of about 0.1% to 1.0%, dissolved in naphtha. A variety of other ink formulations also exist and can find use with the invention. The concentrations of those fight waxes was optimized empirically.

An iron foil having thickness of about 50 microns was laid flat on a clean surface. The PDMS stamp was moisturized with the ink formulation and brought into contact with the iron foil for about 15-20 seconds, then removed.

After application of the protective ink, the stamped iron sheet was then submerged in an etching bath comprising ferric sulfate in a concentration of 15%, although concentrations between 5% and 40% can be used in order to optimize the etching process. The etching will remove iron from the sheet in any location that is not covered by wax, thereby creating a raised relief corresponding to the desired pattern. The etching reaction was stopped by removing the plate from the etching bath and rinsing with water, and then dried.

In some embodiments, ferric sulfate is a preferred etching reagent for metal substrates because it is FDA approved for the animal feed industry and, depending on the concentration of the acid and the temperature of the reaction (which may vary between 15° C. and 60° C.), the etching effect is achieved in less than three minutes. Furthermore, only water is required for cleanup of the acid solution.

Although ferric sulfate is described herein, it is not intended that the invention be limited to the use of ferric sulfate. Other etching acids can also be used, such as nitric acid, phosphoric acid, acetic acid, and their mixtures thereof, and the concentrations of those acids can also be optimized, as known to one of skill in the art. Concentrations of the etching acid can be optimized and may potentially be in a concentration ranging anywhere from 0.1 milliMolar (0.1 mM) to 1.0 Molar (1.0 M).

Figure 5:
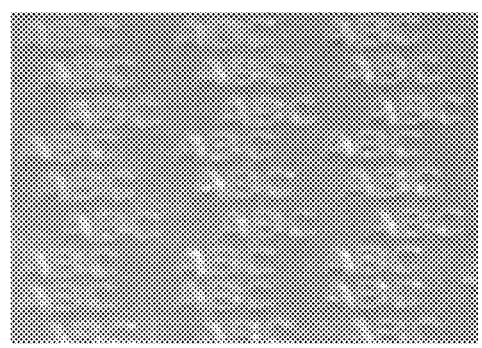
FIG. 5 provides a photomicrograph of an etched iron sheet that was produced using microcontact printing photolithography.

The resulting intact stamped and etched iron foil was visualized using a stereomicroscope using approximately 60× magnification. A field of view was captured in a photomicrograph, as shown in FIG. 5. Each of the A, B and C characters in the field of view is approximately 40 microns in height.

After production of the etched metal foil sheets, the sheets can be ground, as described in EXAMPLE 2, to produce the tracer particles of the invention.

Example 4

Protocol for the Production of Tracer Particles Using Plasma Etching

This example describes methods for producing tracer particles using reactive plasma etching, where exposure to reactive gas plasma accomplishes both the etching of the distinguishing markings on the particles, as well as generating particles of predetermined defined sizes, and where the particles are separated from each other. This methodology incorporates photolithography as one or more intermediate steps during preparation of the particle substrate. A schematic showing the general methodology for plasma etching to generate tracer particles is shown in FIG. 3.

A) Deposition of the Material Stack on the Wafer

A spin-on oxide layer is used to promote liftoff of the finished particles. To manufacture this layer, a clean silicon substrate is placed on a spin coater. A few milliliters of spin-on-oxide solution are put on the wafer, until about 80% of the surface of the wafer is coated with fluid. The spin-coater is then ramped to 500 RPM at a rate of 100 RPM/second and then ramped to 3,000 RPM at a rate of 300 RPM/second. The speed of 3000 RPM is held for ten seconds.

After the layer has been spun onto the wafer, it must be annealed to the silicon substrate. The wafer containing the coating is placed on a hot plate at a temperature of 200° C. for 15 minutes. Then, with the wafer remaining on the hot plate, the temperature of the hot plate is increased to 300° C. The hot plate is maintained at 300° C. for 15 minutes and then allowed to cool to room temperature.

The magnetic polymer layer is then applied to the wafer. A wafer with a silicon oxide liftoff layer already deposited is placed on a spin-coater. About 20 milliliters of polymer solution is dropped onto the center of the wafer and the spin-coater is ramped to 500 RPM at a rate of 100 RPM/second, and then ramped again to 2,000 RPM at a rate of 300 RPM/second. The speed of 2,000 RPM is held for 30 seconds.

Next, a layer of silicon oxide is deposited to act as a hardmask during the etch process. A clean silicon substrate is placed on a spin coater. A few milliliters of spin-on-oxide solution are put on the wafer, until about 80% of the surface of the wafer is coated with fluid. The spin-coater is then ramped to 500 RPM at a rate of 100 RPM/second and then ramped to 3,000 RPM at a rate of 300 RPM/second. The speed of 3000 RPM is maintained for ten seconds.

After the layer has been spun, it must be annealed. The wafer is placed on a hot plate at a temperature of 200° C. for 15 minutes, and then allowed to cool.

The final layer to be added to the material stack is the photoresist layer. This protocol uses SU8-2 photoresist. A wafer that has recently completed the spin-on hardmask step is placed on a spin-coater. Eight (8) mL of photoresist solution are dropped onto the center of the wafer. The spin-coater is then ramped to 500 RPM at a rate of 100 RPM/second and then ramped to 3,000 RPM at a rate of 300 RPM/second. The speed of 3000 RPM is held for 60 seconds.

After spin-coating, the wafer is baked. The wafer is put on a hot plate at a temperature of 65° C. for three minutes. The temperature of the hot plate is then increased to 95° C. and the wafer is allowed to bake for an additional three minutes B) Etching and Microengraving to Produce Tracer Particles The first step in etching the tracer particles is photolithography. In this example, a contact mask is used in the photolithography. The mask is placed on top of the wafer. Care is taken to ensure that there are no air bubbles or gaps between the mask and the wafer. The mask should be placed with the printed side making contact with the wafer.

The wafer is placed under a lamp which emits light at 365 nm. A 350 nm high-pass filter is placed between the lamp and the wafer, and the lamp is turned on for about 10 seconds.

The wafer is developed by placing it in a tub of development solution and agitating it for three minutes. A sonication tool may optionally be used to aid in agitation. The wafer is then dipped into a second tub of fresh development solution and rinsed in isopropanol. If development is incomplete, the isopropanol becomes milky in appearance and the wafer is again placed in the tub of development solution and agitated. After development is complete, the wafer is dried in a stream of nitrogen or compressed air.

A post-exposure bake is used to complete cross-linking of the exposed areas. The wafer is placed on a hot plate, the temperature of the hot plate is increased to 95° C., and the wafer is allowed to remain at temperature for three minutes.

After photolithography is complete, the dielectric hardmask must be etched. This step takes place in a plasma etch chamber. Typically, the wafer is placed in an etch chamber and the vacuum engaged. The pressure in the chamber is allowed to reach 5 mTorr or less before moving on to the next step.

To initiate a plasma reaction and begin the etch process, argon is flowed into the chamber and the throttle valve set so that the pressure in the chamber is 50 millitorr. The RF generator is turned on with a power setpoint of 100 W to strike a plasma. With the plasma remaining on, the gas mixture is changed from 100% Ar to 80% $CF_4$/20% Ar. The gate valve and total flow are adjusted to maintain a pressure of 50 millitorr in the chamber.

The main portion of the etch process uses a higher RF power than the striking portion. The RF power is increased to 200 W and the process is allowed to operate for 120 seconds, or the etch time determined through previous experiments.

Once the dielectric hardmask has been etched, the next step is to etch the magnetic polymer. A 50/50 mixture of argon and oxygen is flowed into the chamber and the throttle valve adjusted such that the pressure in the chamber is 50 mT. The RF generator is activated with a set point of 100 W to strike a plasma.

The main portion of the etch process uses oxygen to oxidize targeted portions of the polymer. The gas mixture is changed from 50/50 Ar/$O_2$ to 95% oxygen/5% carbonyl sulfide and the gate valve and total flow adjusted so that the pressure in the chamber is 20 mT. The plasma should remain on throughout these changes.

Once the gas flows have stabilized, the RF power setpoint is increased to 300 W. The process is allowed to operate for one minute for each three microns of thickness of the magnetic polymer. A sulfur-free gas mixture is used in the final etch step to clean up the edges of the polymer. The gas mixture is changed from 95%/5% oxygen/carbonyl sulfide to 50/50 hydrogen/nitrogen, and the process allowed to operate for 30 seconds. After the proceeding plasma etch steps are complete, the particles have been etched and engraved.

The particles must now be collected, rinsed, dried and stored. The dielectric hardmask and liftoff layer surround the tracer particles like bread in a sandwich. To release the particles, the liftoff and hardmask layers are etched away. To accomplish this, the wafer is placed in a plastic tub with a magnet covered by a plastic bag, the magnet positioned approximately five centimeters above the wafer. A premixed 1M solution of ammonium fluoride is poured into in the tub so that it covers the wafer and the bottom of the magnet. The wafer is then agitated to speed lift-off of the particles. The particles are rinsed with water and then dried.

Example 5

Production of a Pharmaceutical Product Comprising Tracer Particles and Retrieving the Tracer Particles from the Tablet This example describes the production of a pharmaceutical product that incorporates tracer particles. This example uses aspirin to illustrate the principles of how the tracer particles of the invention can be incorporated into any hypothetical drug formulation where the bulk flow materials containing the tracer particles are transformed in the production process to yield a solid formulation such as a tablet. This example also serves to illustrate how magnetic particles can be retrieved, visualized and quantitated from solid pharmaceutical formations, such as tablets.

A) Production of Tracer Particles

A dispersion is made with ethanol (52 ml), ETHOCEL™ ethylcellulose (6.0 g), $TiO_2$ powder (0.5 g) and iron powder (0.3 g, powder size between 1 and 6 micron). Thiamine hydrochloride (0.06 g) is also added and stirring occurs at room temperature for 15 minutes. The dispersion is then used to make 100×100×80 micron ferromagnetic tracer particles with alphanumeric markings 15 microns in height (according to the description in EXAMPLE 3, and elsewhere). Following collection of the finished particles, the density of the resulting particles is approximately 800 particles/mg.

B) Incorporation of Tracer Particles into a Pharmaceutical Formulation

Using a conventional coffee grinder, 300 g of BAYER® Low Dose Aspirin Pain Reliever, 81 milligram enteric coated tablets are ground to a fine powder (e.g., a dry bulk flow particulate material having particles smaller than 149 microns in size or passing through a 100 mesh screen). Each tablet contains 81 mg of the active ingredient acetylsalicylic acid, and in addition, the following inactive ingredients: carnauba wax, corn starch, hypromellose, powdered cellulose and triacetin.

In a container suitable for shaking, 3.0 mg (10 ppm) of ferromagnetic tracer particles are added to 300 g of the ground aspirin tablet powder and the mixture is shaken for 20 minutes. At the end of that time, the uniform powder is placed into a Desktop Pill Press TDP-1.5 (London Fashion Arts Co, Oxfordshire, UK). Using 15 KN of pressure, several hundred aspirin tablets, with a diameter 6 mm and a thickness of 3 mm, are produced within 30 minutes.

C) Isolation and Visualization of Tracer Particles from a Solid Pharmaceutical Formulation Ten (10) grams of the prepared tablets are ground to fine powder (e.g., a dry bulk flow particulate material having particles smaller than 149 microns in size or passing through a 100 mesh screen) using a conventional coffee grinder. The powder is poured into a MicroTracers, Inc., Rotary Detector™ to separate the ferromagnetic tracer particles from the other ingredients (see FIG. 7). The collected tracers (approximately 0.1 mg) are visualized under a stereomicroscope. The observed tracer particles retain the microengraved distinguishing markings, visible at 200× magnification.

To quantitatively evaluate the rate of tracer recovery, the collected ferromagnetic particles are evenly spread on an 18.5 cm diameter filter paper. The filter paper is then sprinkled with a developing solution comprising potassium ferricyanide (0.1 g), 5.5% aqueous solution of potassium hydroxide (2.0 ml), water (20.0 ml) and ethanol (30.0 ml).

The wetted filter paper is transferred to a pre-heated hot plate (100° C.) and heated for 4-5 minutes. Individual tracer particles are counted as bright blue fluorescent spots under a dark camera with UV-light. The described procedure is performed on at least three filter papers to estimate an average amount of retrieved particles.

Using the estimated average, tracer recovery is also evaluated (e.g. 89%) by comparing the actual number of found particles (e.g. 71 particles) and the predicted number of particles that would hypothetically be contained in 0.1 mg pure tracer (e.g. 80 particles). Alternatively, tracer recovery can be evaluated by comparing the actual number of particles recovered from the test sample tablets, to a reference standard tablet containing known numbers of tracer particles, where the reference standard tablets are analyzed in parallel with the test sample tablets using the same methodologies and the same instrumentation.

While the foregoing invention has been described in some detail for purposes of clarity and understanding, it will be clear to one skilled in the art from a reading of this disclosure that various changes in form and detail can be made without departing from the true scope of the invention. It is to be understood that the invention is not limited to any of the specifically recited methodologies, reagents or instrumentation that are recited herein, where similar methodologies, reagents or instrumentation can be substituted and used in the construction and practice of the invention, and remain within the scope of the invention. It is also to be understood that the description and terminology used herein is for the purpose of describing particular embodiments of the invention only, and is not intended that the invention be limited solely to the embodiments described herein.

As used in this specification and the appended claims, singular forms such as "a", "an" and "the" include plural referents unless the content clearly dictates otherwise. For example, reference to "a particle" or "an excipient" also includes a plurality of particles, and combinations of excipients. All industry and technical terms used herein have the same meaning as commonly understood by one of ordinary skill in the art or industry to which the invention pertains, unless defined otherwise.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A population of plasma-etched tracer particles, each particle in the population comprising:
   a) at least one polymer material in admixture with at least one magnetic material, said admixture forming a tracer particle substrate, and
   b) at least one single plasma etched marking on the surface of the tracer particle substrate, wherein each dimension of the single plasma etched marking is smaller than 40 microns, and where each tracer particle in the population has a predetermined fixed width and a predetermined fixed length, where the predetermined width and predetermined length of any one plasma-etched tracer particle in the population is essentially identical to the width and length of at least one other plasma-etched tracer particle in the population;
   where the tracer particle substrate is essentially planar, and each plasma-etched tracer particle in the population is formed by a process that comprises plasma etching the planar substrate in a defined pattern that is the circumference of a single particle to a depth that is the full thickness of the planar substrate, thereby separating individual tracer particles from each other and forming the population of tracer particles.

2. The population of plasma-etched tracer particles of claim 1, wherein the largest dimension of the at least one single plasma etched marking is between 500 nanometers and 20 microns.

3. The population of plasma-etched tracer particles of claim 1, wherein each plasma-etched tracer particle does not exceed about 400 microns in any dimension.

4. The population of plasma-etched tracer particles of claim 1, wherein each plasma-etched tracer particle does not exceed about 100 microns in any dimension.

5. The population of plasma-etched tracer particles of claim 1, wherein the at least one magnetic material is selected from iron, nickel, gamma-ferrioxide and ferrites.

6. The population of plasma-etched tracer particles of claim 1, wherein the at least one single etched marking is an alphanumeric character.

7. The population of plasma-etched tracer particles of claim 1, wherein each plasma-etched tracer particle further comprises a fluorescent material or a thermochromic material.

8. A marked product comprising a population of plasma-etched tracer particles of claim 1.

9. A marked pharmaceutical product comprising the population of plasma-etched tracer particles of claim 1.

10. A marked pharmaceutical product comprising:
   a) at least one excipient,
   b) at least one active ingredient that is dispersed in the excipient, and
   c) a plurality of plasma-etched tracer particles, said tracer particles each comprising
      (i) at least one polymer material in admixture with at least one magnetic material, said admixture forming a tracer particle substrate, and
      (ii) at least one single plasma etched marking-on the surface of tracer particle substrate, wherein each dimension of the at least one single plasma etched marking is smaller than 40 microns, and where each tracer particle has a predetermined fixed width and a predetermined fixed length, where the predetermined width and predetermined length of any one plasma-etched tracer particle is essentially identical to the width and length of at least one other plasma-etched tracer particle in the plurality of particles;
   where the tracer Particle substrate is essentially planar and each plasma-etched tracer particle in the population is formed by process that comprises plasma etching the planar substrate in a defined pattern that is the circumference of a single particle to a depth that is the full thickness of the planar substrate, thereby separating individual tracer particles from each other and forming the plurality of plasma-etched tracer particles,
wherein:
(A) the plurality of plasma-etched tracer particles are dispersed in the excipient, or
(B) the pharmaceutical product is a tablet pharmaceutical product comprising a coating that covers the excipient and active ingredient, wherein the plurality of plasma-etched tracer particles are associated with the coating.

11. The marked pharmaceutical product of claim 10, wherein each particle in the plurality of plasma-etched tracer particles is characterized by an upper size limit, selected from 50 microns, 80 microns, and 100 microns, wherein each plasma-etched tracer particle of the plurality of plasma-etched tracer particles does not exceed the upper size limit in any dimension.

12. The marked pharmaceutical product of claim 10, wherein each plasma-etched tracer particle of the plurality of tracer particles consists essentially of materials generally regarded as safe for human consumption.

13. The marked pharmaceutical product of claim 10, wherein the excipient is selected from solid formulation excipients and liquid formulation excipients.

14. A marked animal feed comprising:
a) an animal feed that is a bulk particulate material, and
b) a plurality of plasma-etched tracer particles that are dispersed in the animal feed, wherein each tracer particle in the plurality of particles comprises (i) at least one polymer material in admixture with at least one magnetic material, said admixture forming a tracer particle substrate, and
(ii) at least one single plasma etched marking on the surface of the tracer particle substrate, wherein each dimension of the at least one single plasma etched marking is smaller than 40 microns, and where each tracer particle has a predetermined fixed width and a predetermined fixed length, where the predetermined width and predetermined length of any one plasma-etched tracer particle is essentially identical to the width and length of at least one other plasma-etched tracer particle in the population;

where the tracer particle substrate is essentially planar, and each plasma-etched tracer particle is formed by a process coma rising plasma etching the planar substrate in a defined pattern that is the circumference of a single particle to a depth that is the full thickness of the planar substrate, thereby separating individual tracer particles from each other and forming the plurality of plasma-etched tracer particles.

15. The marked animal feed of claim 14, wherein each plasma-etched tracer particle in the plurality of particles does not exceed about 350 microns in any dimension.

* * * * *